US012697474B2

(12) United States Patent
Gu et al.

(10) Patent No.: US 12,697,474 B2
(45) **Date of Patent: *Aug. 4, 2026**

(54) CORE-SHELL MICRONEEDLE DEVICES AND USES THEREOF

(71) Applicant: NORTH CAROLINA STATE UNIVERSITY, Raleigh, NC (US)

(72) Inventors: Zhen Gu, Raleigh, NC (US); Jinqiang Wang, Raleigh, NC (US); Yanqi Ye, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 572 days.

This patent is subject to a terminal disclaimer.

(21) Appl. No.: 18/321,936

(22) Filed: May 23, 2023

(65) Prior Publication Data

US 2023/0364402 A1 Nov. 16, 2023

Related U.S. Application Data

(63) Continuation of application No. 16/466,775, filed as application No. PCT/US2017/064723 on Dec. 5, 2017, now Pat. No. 11,697,007.
(Continued)

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 31/728* (2013.01);
(Continued)

(58) Field of Classification Search
CPC .............. A61M 37/00; A61M 37/0015; A61M 2037/0023; A61M 2037/0046; A61M 2037/0061
See application file for complete search history.

(56) References Cited

U.S. PATENT DOCUMENTS

| | | | | |
|---|---|---|---|---|
| 11,697,007 B2 * | 7/2023 | Gu | A61K 38/28 604/173 |
| 2003/0135201 A1 * | 7/2003 | Gonnelli | A61B 5/1486 604/890.1 |

(Continued)

FOREIGN PATENT DOCUMENTS

| | | |
|---|---|---|
| CN | 102281897 | 12/2011 |
| JP | 2005526009 | 9/2005 |

(Continued)

OTHER PUBLICATIONS

International Search Report and Written Opinion in PCT/US2017/064723. Mailed Mar. 29, 2018. 9 pages.

(Continued)

*Primary Examiner* — Laura A Bouchelle
(74) *Attorney, Agent, or Firm* — Meunier Carlin & Curfman LLC

(57) ABSTRACT

The present disclosure relates to microneedle devices and methods for treating a disease (for example, diabetes) using a degradable cross-linked gel for self-regulated delivery of a therapeutic agent (for example, insulin).

18 Claims, 25 Drawing Sheets

Related U.S. Application Data

(60) Provisional application No. 62/430,260, filed on Dec. 5, 2016.

(51) Int. Cl.

| | |
|---|---|
| ***A61K 31/728*** | (2006.01) |
| ***A61K 38/28*** | (2006.01) |
| ***A61K 38/44*** | (2006.01) |
| ***A61K 47/54*** | (2017.01) |
| ***A61K 47/69*** | (2017.01) |
| ***A61P 3/10*** | (2006.01) |

(52) U.S. Cl.

CPC ............. *A61K 38/28* (2013.01); *A61K 38/44* (2013.01); *A61K 47/54* (2017.08); *A61K 47/6955* (2017.08); *A61P 3/10* (2018.01); *A61M 2037/0046* (2013.01); *A61M 2037/0061* (2013.01); *C12Y 101/03004* (2013.01); *C12Y 111/01006* (2013.01)

(56) References Cited

U.S. PATENT DOCUMENTS

| | | | |
|---|---|---|---|
| 2015/0030641 | A1 | 1/2015 | Anderson et al. |
| 2016/0157764 | A1 | 6/2016 | Di Palma |

FOREIGN PATENT DOCUMENTS

| | | |
|---|---|---|
| JP | 2010540507 | 12/2010 |
| JP | 2011508786 | 3/2011 |
| JP | 2016517885 | 6/2016 |
| JP | 2018513874 | 5/2018 |
| WO | 2009040548 | 4/2009 |
| WO | 2013123492 | 8/2013 |
| WO | 2014113679 | 7/2014 |
| WO | 2016172320 | 10/2016 |
| WO | 2016172554 | 10/2016 |
| WO | 2018085809 | 5/2018 |
| WO | 2018106697 | 6/2018 |

OTHER PUBLICATIONS

First Office Action issued in corresponding application No. 201780081305.1, dated Feb. 23, 2021.

Office Action in corresponding JP application No. 2019-529985, mailed Aug. 3, 2021, 4 pages.

Yu Jicheng et al. Microneedle-array patches loaded with hypoxia-sensitive vesicles provide fast glucose-responsive insulin delivery. PNAS Early Edition, 2015, pp. 1-6,p. 3, col. 2, paragraphs 1-2, fig. 4.

Bequette, B.W. A critical assessment of algorithms and challenges in the development of a closed-loop artificial pancreas. Diabetes technology & therapeutics 7, 28-47 (2005).

Bratlie, Kaitlin M., et al. "Materials for diabetes therapeutics." Advanced healthcare materials 1.3 (2012): 267-284.

Broom, W.A., Coulthard, C.E., Gurd, M.R. & Sharpe, M.E. Some pharmacological and chemotherapeutic properties of notatin. British Journal of Pharmacology and Chemotherapy 1, 225-233 (1946).

Burns, Nancy A., et al. "Nanodiamond gels in nonpolar media: Colloidal and rheological properties." Journal of Rheology 58.5 (2014): 1599-1614.

Cengiz, E., Sherr, J.L., Weinzimer, S.A. & Tamborlane, W.V. New-generation diabetes management: glucose sensor-augmented insulin pump therapy. Expert review of medical devices 8, 449-458 (2011).

Chou, D.H. et al. Glucose-responsive insulin activity by covalent modification with aliphatic phenylboronic acid conjugates. Proceedings of the National Academy of Sciences of the United States of America 112, 2401-2406 (2015).

Davis, S.P., Landis, B.J., Adams, Z.H., Allen, M.G. & Prausnitz, M.R. Insertion of microneedles into skin: measurement and prediction of insertion force and needle fracture force. Journal of biomechanics 37, 1155-1163 (2004).

De Duve, C. & Baudhuin, P. Peroxisomes (microbodies and related particles). Physiological Reviews 46, 323-357 (1966).

Dong, Yizhou, et al. "Injectable and glucose-responsive hydrogels based on boronic acid-glucose complexation." Langmuir 32.34 (2016): 8743-8747.

Gordijo, Claudia R., et al. "Nanotechnology-enabled closed loop insulin delivery device: In vitro and in vivo evaluation of glucose-regulated insulin release for diabetes control." Advanced Functional Materials 21.1 (2011): 73-82.

Gu, Z. et al. Glucose-responsive microgels integrated with enzyme nanocapsules for closed-loop insulin delivery. ACS nano 7, 6758-6766 (2013).

Gu, Z. et al. Injectable nano-network for glucose-mediated insulin delivery. ACS nano 7, 4194-4201 (2013).

Hassan, C.M., Doyle, F.J. & Peppas, N.A. Dynamic Behavior of Glucose-Responsive Poly(methacrylic acid-g-ethylene glycol) Hydrogels. Macromolecules 30, 6166-6173 (1997).

Jin, X.J. et al. Prevention of UV-induced skin damages by 11,14,17-eicosatrienoic acid in hairless mice in vivo. Journal of Korean medical science 25, 930-937 (2010).

Joel, S., Turner, K.B. & Daunert, S. Glucose Recognition Proteins for Glucose Sensing at Physiological Concentrations and Temperatures. ACS Chemical Biology 9, 1595-1602 (2014).

Kataoka, K., Miyazaki, H., Bunya, M., Okano, T. & Sakurai, Y. Totally synthetic polymer gels responding to external glucose concentration: their preparation and application to on-off regulation of insulin release. Journal of the American Chemical Society 120, 12694-12695 (1998).

Kitano, S., Koyama, Y., Kataoka, K., Okano, T. & Sakurai, Y. A novel drug delivery system utilizing a glucose responsive polymer complex between poly (vinyl alcohol) and poly (N-vinyl-2-pyrrolidone) with a phenylboronic acid moiety. Journal of Controlled Release 19, 161-170 (1992).

Lee, I.C., He, J.-S., Tsai, M.-T. & Lin, K.-C. Fabrication of a novel partially dissolving polymer microneedle patch for transdermal drug delivery. Journal of Materials Chemistry B 3, 276-285 (2015).

Liu, F., Song, S.C., Mix, D., Baudyš, M. & Kim, S.W. Glucose-Induced Release of Glycosylpoly(ethylene glycol) Insulin Bound to a Soluble Conjugate of Concanavalin A. Bioconjugate Chemistry 8, 664-672 (1997).

Liu, X. et al. Fusogenic Reactive Oxygen Species Triggered Charge-Reversal Vector for Effective Gene Delivery. Advanced materials 28, 1743-1752 (2016).

Liu, Y. et al. Biomimetic enzyme nanocomplexes and their use as antidotes and preventive measures for alcohol intoxication. Nat Nano 8, 187-192 (2013).

Major Jourden, J.L. & Cohen, S.M. Hydrogen peroxide activated matrix metalloproteinase inhibitors: a prodrug approach. Angewandte Chemie 49, 6795-6797 (2010).

Matsumoto, A., Kurata, T., Shiino, D. & Kataoka, K. Swelling and Shrinking Kinetics of Totally Synthetic, Glucose-Responsive Polymer Gel Bearing Phenylborate Derivative as a Glucose-Sensing Moiety. Macromolecules 37, 1502-1510 (2004).

Matsumoto, A., Yoshida, R. & Kataoka, K. Glucose-responsive polymer gel bearing phenylborate derivative as a glucose-sensing moiety operating at the physiological pH. Biomacromolecules 5, 1038-1045 (2004).

Mo, R., Jiang, T., Di, J., Tai, W. & Gu, Z. Emerging micro- and nanotechnology based synthetic approaches for insulin delivery. Chemical Society reviews 43, 3595-3629 (2014).

Ohkubo, Y et al. Intensive insulin therapy prevents the progression of diabetic microvascular complications in Japanese patients with non-insulin-dependent diabetes mellitus: a randomized prospective 6-year study. Diabetes research and clinical practice 28, 103-117 (1995).

Olatunji, Ololade, et al. Influence of array interspacing on the force required for successful microneedle skin penetration: theoretical and practical approaches. Journal of pharmaceutical sciences 102.4 (2013): 1209-1221.

Owens, David R., Bernard Zinman, and Geremia B. Bolli. "Insulins today and beyond." The lancet358.9283 (2001): 739-746.

(56) References Cited

OTHER PUBLICATIONS

Piest, M., Zhang, X.L., Trinidad, J. & Engbersen, J.F.J. pH-responsive, dynamically restructuring hydrogels formed by reversible crosslinking of PVA with phenylboronic acid functionalised PPO-PEO-PPO spacers (Jeffamines (R)). Soft Matter 7, 11111-11118 (2011).
Podual, K., Doyle Iii, F.J. & Peppas, N.A. Glucose-sensitivity of glucose oxidase-containing cationic copolymer hydrogels having poly(ethylene glycol) grafts. Journal of Controlled Release 67, 9-17 (2000).
Saravanakumar, G., Kim, J. & Kim, W.J. Reactive-Oxygen-Species-Responsive Drug Delivery Systems: Promises and Challenges. Advanced Science (2016), 1600124.
Shiino, D. et al. Amine containing phenylboronic acid gel for glucose-responsive insulin release under physiological pH. Journal of controlled release 37, 269-276 (1995).
Springsteen, G. & Wang, B. A detailed examination of boronic acid-diol complexation. Tetrahedron 58, 5291-5300 (2002).
Tai, W. et al. Bio-inspired synthetic nanovesicles for glucose-responsive release of insulin. Biomacromolecules 15, 3495-3502 (2014).
Veiseh, O., Tang, B.C., Whitehead, K.A., Anderson, D.G. & Langer, R. Managing diabetes with nanomedicine: challenges and opportunities. Nature reviews. Drug discovery 14, 45-57 (2015).
Wang, M., Sun, S., Neufeld, C.I., Perez-Ramirez, B. & Xu, Q. Reactive oxygen species-responsive protein modification and its intracellular delivery for targeted cancer therapy. Angewandte Chemie 53, 13444-13448 (2014).
Yamamoto, Y., Koma, H. & Yagami, T. Hydrogen peroxide mediated the neurotoxicity of an antibody against plasmalemmal neuronspecific enolase in primary cortical neurons. NeuroToxicology 49, 86-93 (2015).
Yu, J. et al. Microneedle-array patches loaded with hypoxia-sensitive vesicles provide fast glucose-responsive insulin delivery. Proceedings of the National Academy of Sciences of the United States of America 112, 8260-8265 (2015).
Zhang, K. & Wu, X.Y. Modulated insulin permeation across a glucose-sensitive polymeric composite membrane. Journal of controlled release 80, 169-178 (2002).
International Report on Patentability issued for Application No. PCT/US2017/064723, dated Jun. 20, 2019.

* cited by examiner

CORE-SHELL MICRONEEDLE DEVICES AND USES THEREOF

CROSS REFERENCE TO RELATED APPLICATIONS

This application is a continuation of U.S. Non-Provisional patent application Ser. No. 16/466,775 filed Jun. 5, 2019, which is a national stage application filed under 35 U.S.C. § 371 of PCT/US2017/064723 filed Dec. 5, 2017, which claims the benefit of U.S. Provisional Patent Application Ser. No. 62/430,260 filed Dec. 5, 2016, the disclosures of which are expressly incorporated herein by reference.

STATEMENT REGARDING FEDERALLY SPONSORED RESEARCH

This invention was made with government support under grant number TR001111 awarded by the National Institutes of Health. The government has certain rights in the invention.

FIELD

The present disclosure relates to microneedle devices and methods for treating a disease (for example, diabetes) using a degradable cross-linked gel for self-regulated delivery of a therapeutic agent (for example, insulin).

BACKGROUND

Diabetes mellitus, a chronic disease affecting 422 million people worldwide in 2016, is characterized by a deficit of endogenously-produced insulin and elevated blood glucose levels (BGLs). In the absence of proper control, chronically elevated BGLs can lead to limb amputation, blindness, kidney failure and cardiovascular disease. To prevent these diabetic complications, patients with type 1 and advanced type 2 diabetes use injected or infused insulin generally fail to reach targets and with the aim to achieve normoglycemia. However, open-loop exogenous insulin injections or infusion generally fail to reach targets and carries the additional risk of hypoglycemia when insulin levels exceed that needed; these hypoglycemic episodes can be severe and even lethal. Therefore, there is an urgent need for a bio-inspired "artificial β-cell" system that can intelligently "secrete" desirable amounts of insulin in response to elevated BGLs while maintaining basal insulin release kinetics at normoglycemia.

To this end, closed-loop device-based systems have been developed and integrate patient-calibrated continuous glucose-monitoring sensor and an external insulin infusion pump. However, such systems remain challenged in terms of algorithm accuracy and sensor reliability. Therefore, chemically-engineered formulations or devices that can swell, degrade, or dissociate in response to ambient elevated BGLs have attracted increasing attention as an alternate solution. These systems typically employ one of three different materials and corresponding mechanisms of actions, including glucose oxidase (GOx), phenylboronic acid (PBA), and glucose binding proteins (GBP). GOx catalyzes the oxidation of D-glucose to D-gluconolactone, which can hydrolyze to gluconic acid, and generate hydrogen peroxide in the presence of oxygen:

$$\text{Glucose} + O_2 + H_2O \xrightarrow{GO_x} \text{Gluconic acid} + H_2O_2$$

Accordingly, acidity-sensitive systems entrapping GOx can create a local acidic environment in response to elevated glucose levels to trigger the release of insulin. However, it is highly challenging to rapidly switch the physiological pH in vivo to achieve fast response. A hypoxia-sensitive formulation to achieve fast response was developed based on the enzymatic consumption of local oxygen level. However, this formulation is limited by the hydrogen peroxide that remains in this system raising concerns over long-term biocompatibility. Moreover, the simultaneous release of GOx with insulin has the potential to cause systemic toxicity. Moving forward, the next generation of smart insulin delivery should be developed to prioritize rapid responsiveness, ease of preparation and administration, and excellent biocompatibility.

The compositions, devices, microneedle patches, and methods disclosed herein address these and other concerns.

SUMMARY

Disclosed herein is a bio-inspired glucose-responsive therapeutic agent (for example, insulin) delivery system for self-regulation of blood glucose levels. The compositions and methods disclosed herein are desirable for improving health and quality of life outcomes for type 1 and advanced type 2 diabetic patients. In some embodiments, disclosed herein is a painless core-shell microneedle array patch consisting of degradable crosslinked gel for smart delivery of a therapeutic agent with rapid responsiveness and excellent biocompatibility. This gel-based device can partially dissociate and subsequently release the therapeutic agent (for example, insulin) when triggered by $H_2O_2$ generated during the oxidation of glucose by a glucose-specific enzyme embedded inside the gel. Importantly, the $H_2O_2$-responsive microneedles are coated with a thin layer embedding $H_2O_2$-scavenging enzyme, thus mimicking the complementary function of enzymes in peroxisomes to protect normal tissues from injury caused by oxidative stress. Utilizing a chemically-induced type 1 diabetic mouse model, this smart insulin patch with a bio-responsive core and protective shell is shown to effectively regulate blood glucose levels within a normal range with negligible long-term side effects.

In some aspects, disclosed herein is a microneedle patch, comprising:

- a plurality of microneedles each having a base end and a tip; and
- a substrate to which the base ends of the microneedles are attached;
- wherein the microneedles comprise:
  - a shell, comprising:
    - a first poly(vinyl alcohol) (PVA) polymer cross-linked with a first peroxide-sensitive linker; and
    - a peroxide scavenging enzyme encapsulated within a first nanogel, wherein the first nanogel is embedded in the first PVA polymer;
  - and
  - a core, comprising:
    - a second poly(vinyl alcohol) (PVA) polymer cross-linked with a second peroxide-sensitive linker;
    - a glucose-responsive agent encapsulated within a second nanogel, wherein the second nanogel is embedded in the second PVA polymer; and
    - a therapeutic agent, wherein the therapeutic agent is covalently attached to the second PVA polymer with a third peroxide-sensitive linker.

In some embodiments, the first peroxide-sensitive linker comprises a boronic ester. In some embodiments, the first peroxide-sensitive linker detaches from the first PVA polymer upon exposure to peroxide. In some embodiments, the first peroxide-sensitive linker is N1-(4-boronobenzyl)-N3-(4-boronophenyl)-N1,N1,N3,N3-tetramethylpropane-1,3-diaminium (TSPBA).

In some embodiments, the second peroxide-sensitive linker comprises a boronic ester. In some embodiments, the second peroxide-sensitive linker detaches from the second PVA polymer upon exposure to peroxide. In some embodiments, the second peroxide-sensitive linker is N1-(4-boronobenzyl)-N3-(4-boronophenyl)-N1,N1,N3,N3-tetramethylpropane-1,3-diaminium (TSPBA).

In some embodiments, the third peroxide-sensitive linker comprises a boronic ester. In some embodiments, the third peroxide-sensitive linker detaches from the second PVA polymer upon exposure to peroxide. In some embodiments, the third peroxide-sensitive linker is 4-nitrophenyl-(4,4,5,5-tetramethyl-1,3,2-dioxaborolan-2-yl)benzyl carbonate (NBC).

In some embodiments, the glucose-responsive agent comprises glucose oxidase. In some embodiments, the peroxide scavenging enzyme is catalase. In some embodiments, the therapeutic agent is insulin. In some embodiments, the microneedles further comprise hyaluronic acid (HA).

In some aspects, disclosed herein is a method of delivering a therapeutic agent to a subject, comprising:

administering to the subject a microneedle patch as disclosed herein; and releasing the therapeutic agent from the microneedle patch in the presence of hyperglycemic levels of glucose.

In some embodiments, the subject has hyperglycemia.

In some embodiments, the glucose-responsive agent produces a peroxide when exposed to hyperglycemic levels of glucose. In some embodiments, the method further comprises detaching the first peroxide-sensitive linker from the first PVA polymer upon exposure to the peroxide.

In some embodiments, the method further comprises detaching the third peroxide-sensitive linker from the second PVA polymer upon exposure to the peroxide. In some embodiments, the detaching of the third peroxide-sensitive linker from the second PVA polymer releases the therapeutic agent from the microneedle patch.

In some embodiments, the method further comprises reducing blood glucose levels. In some embodiments, the therapeutic agent comprises insulin. In some embodiments, the method further comprises terminating release of the therapeutic agent prior to causing hypoglycemia.

The details of one or more embodiments of the invention are set forth in the accompanying drawings and the description below. Other features, objects, and advantages of the invention will be apparent from the description and drawings, and from the claims.

DESCRIPTION OF DRAWINGS

The accompanying figures, which are incorporated in and constitute a part of this specification, illustrate several aspects described below.

FIG. 1A, Insulin release was triggered by the hyperglycemic state from PVA-TSPBA microneedle patch and local inflammation was greatly reduced by the catalase (CAT) embedded PVA-TSPBA shell. FIG. 1B, Insulin modified with 4-nitrophenyl-(4,4,5,5-tetramethyl-1,3,2-dioxaborolan-2-yl)benzyl carbonate (NBC) and the mechanism of $H_2O_2$ responsive release. FIG. 1C, Fabrication and the $H_2O_2$ responsiveness of PVA-TSPBA gels.

FIG. 2A, Insulin release from PVA-TSPBA gels in PBS with 10 mM $H_2O_2$ at pH 7.4 and 3.5. FIG. 2B, Glucose concentration dependent $H_2O_2$ generation in PBS 7.4 in the presence of glucose oxidase (GOx). GOx was directly added to solution to 0.2 mg/mL. FIG. 2C, Glucose concentration dependent insulin release from gels in PBS 7.4 in the presence of GOx. GOx was directly added to solution to 0.2 mg/mL. The glucose concentration was set as 0, 100 and 400 mg/dL. FIG. 2D, the glucose dependent change of gels in PBS 7.4 with GOx (0.2 mg/mL). FIG. 2E, Self-regulated insulin release profile as a function of glucose concentration. FIG. 2F, Pulsatile insulin release profile as a function of glucose concentration.

FIG. 3A, Representative fluorescence microscopy images of insulin loaded MN arrays with hyaluronic acid (HA) base. Rhodamine B labeled insulin was loaded in PVA-TSPBA gel at the top of microneedles (red) while the HA base (green, labeled by FITC-insulin) was mainly located at the bottom. FIG. 3B, Representative fluorescence image of MN array patch loaded with insulin-FITC. Scale bars, 300 μm. FIG. 3C, Representative scanning electron microscopy image of microneedle patch. scale bar, 300 μm. FIG. 3D, Mechanical strength of MNs; FIG. 3E, Representative images of bottom view of hollow CAT loaded MNs. These images were obtained using confocal laser scanning microscopy and the intervals at z-direction were set as 100 μm. Scale bar, 300 μm. FIG. 3F, Representative images of cross-section of core-shell MN using cryosection: rhodamine B labeled CAT shell (red), FITC labeled insulin (green) and their overlap. The shell was 10 μm thick as analyzed using imageJ. FIG. 3G, The time dependent release of GOx or GOx-nanogel (GOx-NG) from PVA methyl acryl ate gel.

FIG. 4A, Mice treated with a MN array patch (left), and the skin inserted by MN array patch was excised and stained using trypan blue (right). Scale bar, 600 μm. FIG. 4B, Representative images of core-shell MNs inserted into skins: the shell embedding rhodamine B labeled CAT (red), the core labeled by insulin-FITC (green) and their overlap. Scale bar, 100 μm. FIG. 4C, Blood glucose levels of type 1 diabetic mice treated with different kinds of microneedle array patches. FIG. 4D, In vivo glucose tolerance test toward diabetic mice at one hour post-treatment of MN-CAT or subcutaneously injected with insulin. Healthy mice were used as the control. FIG. 4E, Responsiveness was calculated based on the area under the curve (AUC) in 120 min, with the baseline set at the 0-min blood glucose reading. FIG. 4F, Blood glucose levels change of healthy mice treated with MN array patch or subcutaneously injected insulin. The treatment was given at 0 min. FIG. 4G, Quantification of the hypoglycemia index, identified as the difference between the initial and nadir blood glucose readings divided by the time at which nadir was reached. FIG. 4H, Blood glucose levels change of diabetic mice treated with multiple MN-array patches. The administration of MN-CAT was indicated by blue arrows. Each time, there were two microneedles on mice except the first one, and the last two microneedles were removed as indicated by red arrows. Student's t-test: **P<0.01. Data points represent mean±SD (n=5). Error bars indicate SD.

FIG. 5A, Representative images of skins at the treated site of mice and their corresponding H&E staining results. Mice were treated with MN-Gel, MN-Gel(G+I), MN-Gel(G+C+I), and MN-CAT. Scale bar, 1 mm or 300 μm for mice skin images and H&E staining respectively. FIG. 5B, Statistical analysis of the thickness of epidermis and skin treated by MNs. The epidermis and skin treated by MN-CAT showed significantly less swelling than that treated with MN-Gel(G+I) (**P<0.01). FIG. 5C, Immunohistology stain with TUNEL assay (green) and Hoechst (blue) of skins treated with MN-Gel (G+I), MN-Gel(G+C+I) and MN-CAT. Scale bars, 150 μm.

FIG. 7A) before oxidation; FIG. 7B) after oxidation in 10 mM $H_2O_2$ in 1 h.

FIG. 9A) Frequency spectra of the elastic (G') and viscous (G") moduli of PVA and PVA-TSPBA samples, with the former exhibiting solution-like characteristics and the latter a gel-like behavior. FIG. 9B) Evolution of G' and G" as a function of time of the PVA-TSPBA sample showing sol-gel transition. Experiments were at a constant frequency of 5 rad/s. Measurements were started after pre-shear the sample for 10 s at a shear rate of 10 s−1.

FIG. 11A) The size distribution of CAT and CAT-NG measured by dynamic laser scattering. FIG. 11B) The representative TEM images of CAT-NG.

FIG. 12A) The size distribution of GOx and GOx-NG measured by dynamic laser scattering. FIG. 12B) The representative TEM image of GOx-NG.

DETAILED DESCRIPTION

Figure 1A:
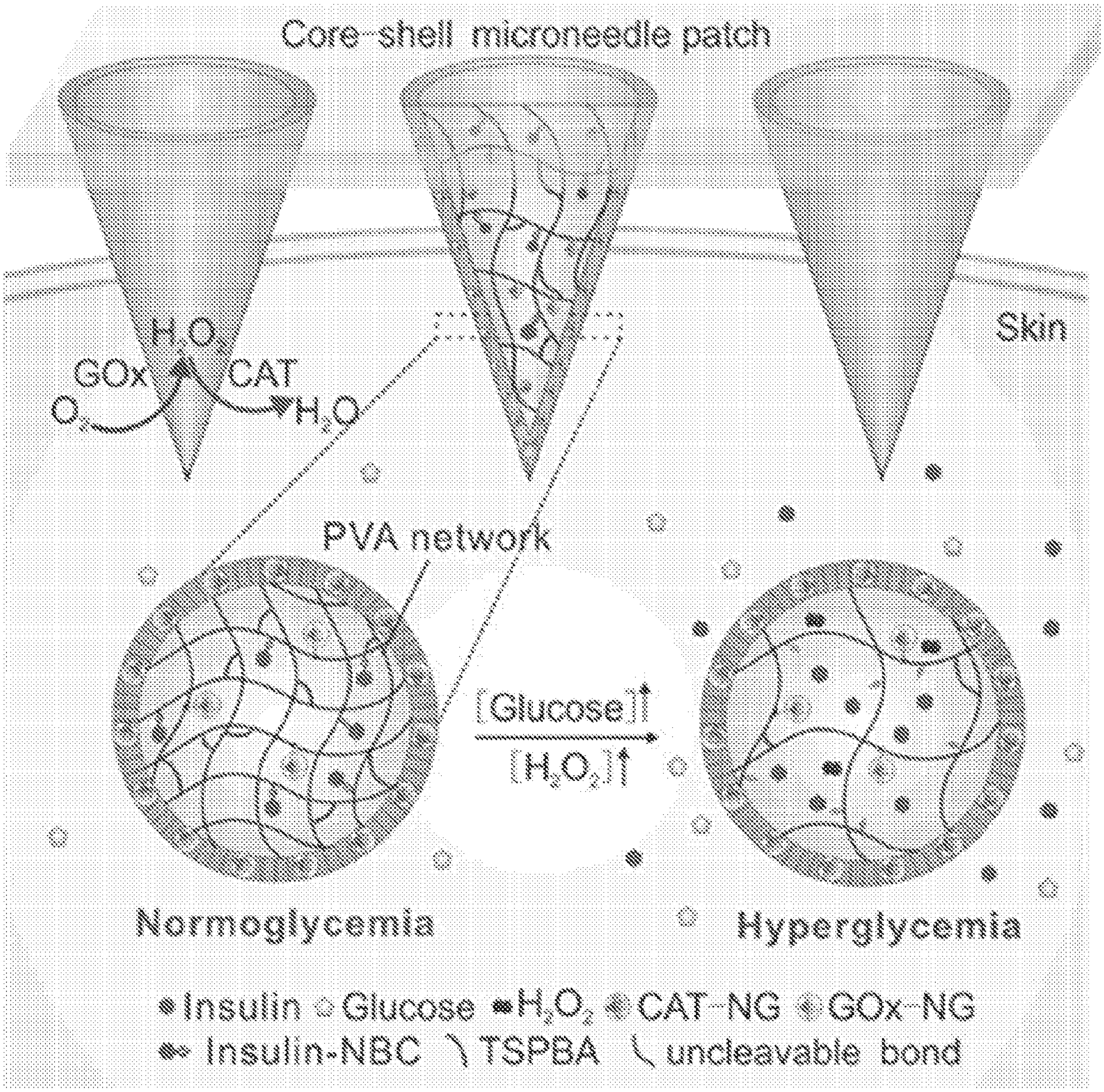
FIGS. 1A-1C. Schematic representation of the glucose-responsive insulin delivery system using $H_2O_2$ responsive poly(vinyl alcohol)—N1-(4-boronobenzyl)-N3-(4-boronophenyl)-N1,N1,N3,N3-tetramethylpropane-1,3-diaminium (PVA-TSPBA) gel.
Figure 6:
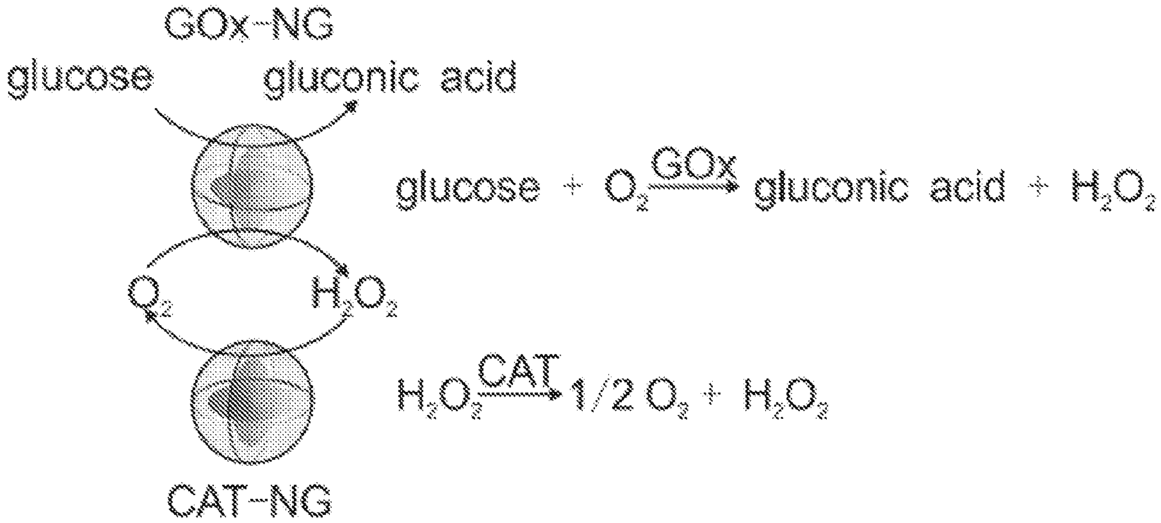
FIG. 6. Schematic illustration of $H_2O_2$ generation by glucose oxidase nanogel (GOx-NG) and elimination by catalase nanogel (CAT-NG).

Disclosed herein is an innovative core-shell microneedle (MN) array patch consisting of degradable crosslinked poly (vinyl alcohol) (PVA) gel for self-regulated delivery of a therapeutic agent (for example insulin) with rapid responsiveness to elevated blood glucose levels (BGLs). As shown in FIG. 1*a*, a core component of this device contains glucose oxidase (GOx) that generates $H_2O_2$ to stimulate release of the therapeutic agent, such as insulin, while the shell component is embedded with catalase (CAT) that serves as an active strainer to scavenge excessive $H_2O_2$, thus minimizing the risk of inflammation caused by $H_2O_2$ (FIG. 6).

Figure 1B:
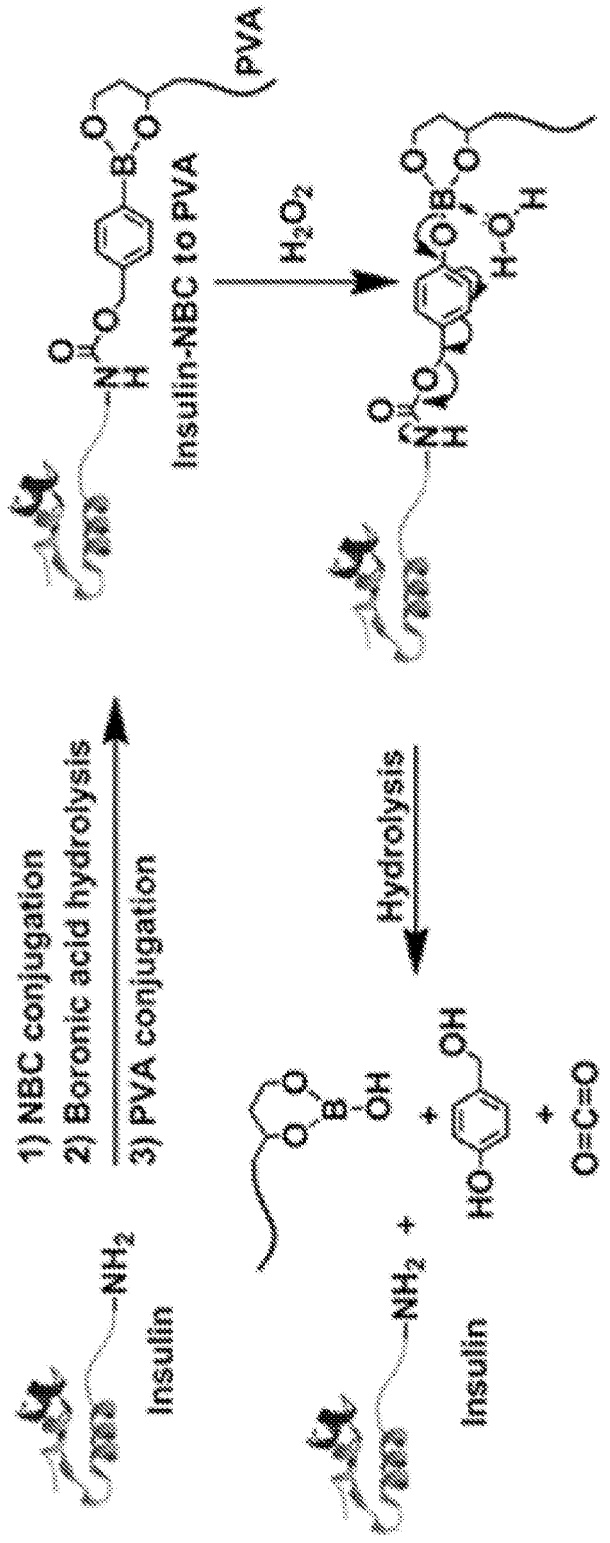
Figure 1C:
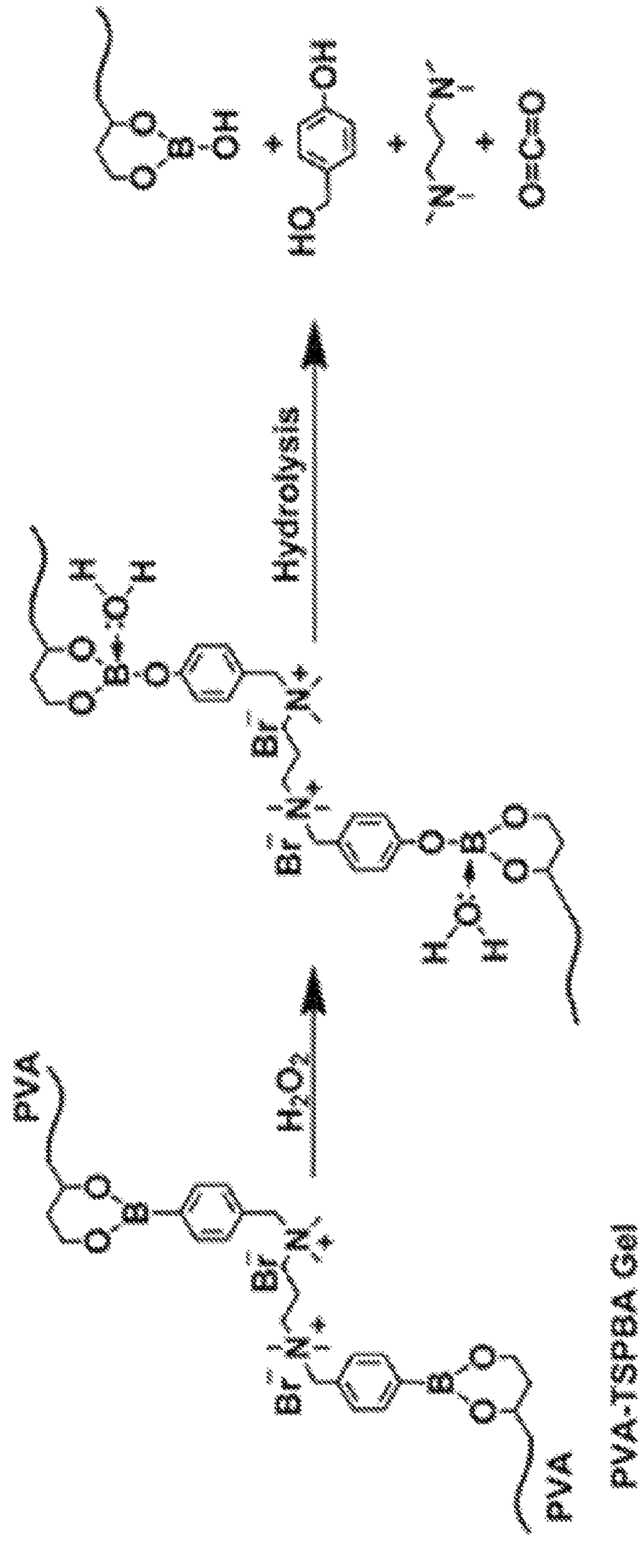

To achieve $H_2O_2$-responsive insulin release, insulin is chemically modified with 4-nitrophenyl4-(4,4,5,5-tetramethyl-1,3,2-dioxaborolan-2-yl) benzyl carbonate (designated insulin-NBC, FIG. 1*b*) and subsequently anchored to the water-soluble PVA matrix.[17] Of note, to further facilitate transport of free insulin in the polymeric matrix and promote responsiveness speed, PVA is also gelated by a $H_2O_2$-labile linker: N1-(4-boronobenzyl)-N3-(4-boronophenyl)-N1,N1,N3,N3-tetramethylpropane-1,3-diaminium (TSPBA) (FIG. 1*c*). Both insulin-NBC and TSPBA are oxidized and hydrolyzed when exposed to local elevated levels of $H_2O_2$ generated by GOx in high glucose concentrations [18, 19], leading to the quick release of free insulin (FIG. 1*a*).

To limit the potentially harmful release of GOx itself [16], GOx is encapsulated into the acrylated nanogel (GOx-NG) to acquire a large size[8] and get immobilized with covalent linkage to PVA methacrylate during radical polymerization, which forms a partially uncleavable network of PVA to further prevent the leakage of GOx-NG while maintaining ease of insulin release. The shell component is designed to mimic the complementary function in peroxisome[20] where catalase nanogel (CAT-NG)[8] is formed and embedded inside a crosslinked PVA layer covering the surface of PVA-TSPBA microneedle core.

Collectively, the design of the core and shell components offers: 1) sufficient catalysis with GOx to perform the glucose-responsive action in the core; and 2) efficient elimination of $H_2O_2$, to alleviate inflammation affecting the surrounding tissues and mitigate systemic toxicity. Additionally, the direct conjugation method that is utilized to load insulin onto the MN scaffold enhances both efficiency and capacity of the insulin-loading process. Upon painless transcutaneous administration, this bio-responsive MN patch partially dissolves when exposed to high interstitial fluid glucose concentration in the capillary networks,[9] thereby releasing insulin for quick uptake through the regional capillary vessels and lymph networks to subsequently regulate BGLs.[9]

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meaning as commonly understood to one of ordinary skill in the art to which this invention belongs. The following definitions are provided for the full understanding of terms used in this specification.

Terminology

Unless defined otherwise, all technical and scientific terms used herein have the same meaning as commonly understood to one of ordinary skill in the art to which this disclosure belongs. The term "comprising" and variations thereof as used herein is used synonymously with the terms "including," "containing," and variations thereof and are open, non-limiting terms. Although the terms "comprising," "including," and "containing" have been used herein to describe various embodiments, the terms "consisting essentially of" and "consisting of" can be used in place of "comprising," "including," and "containing" to provide for more specific embodiments and are also disclosed.

Disclosed are the components to be used to prepare the disclosed compositions, devices, and patches, as well as the compositions, devices, and patches themselves to be used within the methods disclosed herein. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a particular composition or device is disclosed and discussed and a number of modifications that can be made are discussed, specifically contemplated is each and every combination and permutation and the modifications that are possible unless specifically indicated to the contrary. Thus, if a class of components A, B, and C are disclosed as well as a class of components D, E, and F and an example of a combination, or, for example, a combination comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions, devices, and patches. Thus, if there are a variety of additional steps that can be performed it is understood that each of these additional steps can be performed with any specific embodiment or combination of embodiments of the disclosed methods.

It is understood that the components, compositions, devices, and patches disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

The term "administering" refers to an administration to a subject that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques.

"Biocompatible" generally refers to a material and any metabolites or degradation products thereof that are generally non-toxic to the recipient and do not cause any significant adverse effects to the subject.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

As used herein, "conjugated" refers to a non-reversible binding interaction.

A "linker" as used herein refers to a molecule that joins adjacent molecules. Generally, a linker has no specific biological activity other than to join the adjacent molecules or to preserve some minimum distance or other spatial relationship between them. In some cases, the linker can be selected to influence or stabilize some property of the adjacent molecules, such as the folding, net charge, or hydrophobicity of the molecule. In some embodiments, the linker can be detached (e.g. chemically cleaved) upon exposure to a peroxide, such as hydrogen peroxide. In other embodiments, the linker can remain intact upon exposure to a peroxide, such as hydrogen peroxide.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

Microneedle Devices (Patches)

Disclosed herein is an innovative self-regulated microneedle (MN) patch for the delivery of a therapeutic agent (for example, insulin).

In some aspects, disclosed herein is a microneedle patch, comprising:

a plurality of microneedles each having a base end and a tip; and a substrate to which the base ends of the microneedles are attached;

wherein the microneedles comprise:

a shell, comprising:

a first poly(vinyl alcohol) (PVA) polymer crosslinked with a first peroxide-sensitive linker; and a peroxide scavenging enzyme encapsulated within a first nanogel, wherein the first nanogel is embedded in the first PVA polymer;

and a core, comprising:

a second poly(vinyl alcohol) (PVA) polymer crosslinked with a second peroxide-sensitive linker;

a glucose-responsive agent encapsulated within a second nanogel, wherein the second nanogel is embedded in the second PVA polymer; and a therapeutic agent, wherein the therapeutic agent is covalently attached to the second PVA polymer with a third peroxide-sensitive linker.

In some embodiments, the first peroxide-sensitive linker comprises a boronic ester. In some embodiments, the first peroxide-sensitive linker detaches from the first PVA polymer upon exposure to peroxide. In some embodiments, the first peroxide-sensitive linker is N1-(4-boronobenzyl)-N3-(4-boronophenyl)-N1,N1,N3,N3-tetramethylpropane-1,3-diaminium (TSPBA).

In some embodiments, the second peroxide-sensitive linker comprises a boronic ester. In some embodiments, the second peroxide-sensitive linker detaches from the second PVA polymer upon exposure to peroxide. In some embodiments, the second peroxide-sensitive linker is N1-(4-boronobenzyl)-N3-(4-boronophenyl)-N1,N1,N3,N3-tetramethylpropane-1,3-diaminium (TSPBA).

In some embodiments, the third peroxide-sensitive linker comprises a boronic ester. In some embodiments, the third peroxide-sensitive linker detaches from the second PVA polymer upon exposure to peroxide. In some embodiments, the third peroxide-sensitive linker is 4-nitrophenyl-(4,4,5,5-tetramethyl-1,3,2-dioxaborolan-2-yl)benzyl carbonate (NBC).

In some embodiments, the peroxide-sensitive linker comprises 4-nitrophenyl-(4,4,5,5-tetramethyl-1,3,2-dioxaborolan-2-yl)benzyl carbonate (NBC) or N1-(4-boronobenzyl)-N3-(4-boronophenyl)-N1,N1,N3,N3-tetramethylpropane-1,3-diaminium (TSPBA).

In some embodiments, the glucose-responsive agent comprises glucose oxidase. In some embodiments, the peroxide scavenging enzyme is catalase. In some embodiments, the glucose-responsive agent is encapsulated within a nanogel. In some embodiments, the glucose-responsive agent is covalently attached to the nanogel. In some embodiments, the peroxide scavenging enzyme is encapsulated within a nanogel. In some embodiments, the peroxide scavenging enzyme is covalently attached to the nanogel. In some embodiments, the microneedles are coated with the peroxide scavenging enzyme.

Examples of peroxide ($H_2O_2$) scavenging enzymes include, but are not limited to catalase, phenolic acid, 3,4,5-trihydroxybenzoic (gallic) acid and 1,2,3-trihydroxybenzene (pyrogallol). The $H_2O_2$ scavenging enzymes can be incorporated into the microneedle by any means known in the art, including incorporation of the $H_2O_2$ scavenging enzyme in a nanogel (for example a peroxisome catalase nanogel).

In some embodiments, the first nanogel comprises a methacrylate nanogel. In some embodiments, the first nanogel comprises poly(vinyl alcohol) (PVA) methacrylate.

In some embodiments, the second nanogel comprises a methacrylate nanogel. In some embodiments, the second nanogel comprises poly(vinyl alcohol) (PVA) methacrylate.

In some embodiments, the nanogels disclosed herein are embedded within a crosslinked PVA polymer. In some embodiments, the nanogels disclosed herein are covalently linked to a crosslinked PVA polymer. In some embodiments, the first nanogel is embedded in the first PVA polymer. In some embodiments, the first nanogel is covalently attached to the first PVA polymer. In some embodiments, the second nanogel is embedded in the second PVA polymer. In some embodiments, the second nanogel is covalently attached to the second PVA polymer.

In some embodiments, the covalent attachment is via a non-cleavable covalent bond.

In some embodiments, the therapeutic agent is insulin. In some embodiments, the microneedles further comprise hyaluronic acid (HA).

In some aspects, disclosed herein is a device for transport of a material across a biological barrier of a subject comprising:

a plurality of microneedles each having a base end and a tip;

a substrate to which the base ends of the microneedles are attached or integrated; and wherein the microneedles comprise:

a shell, comprising:

a first poly(vinyl alcohol) (PVA) polymer crosslinked with a first peroxide-sensitive linker; and a peroxide scavenging enzyme encapsulated within a first nanogel, wherein the first nanogel is embedded in the first PVA polymer;

and a core, comprising:

a second poly(vinyl alcohol) (PVA) polymer crosslinked with a second peroxide-sensitive linker;

a glucose-responsive agent encapsulated within a second nanogel, wherein the second nanogel is embedded in the second PVA polymer; and a therapeutic agent, wherein the therapeutic agent is covalently attached to the second PVA polymer with a third peroxide-sensitive linker.

In further aspects, also disclosed herein is a kit of parts for delivering a therapeutic agent (for example, insulin) across a biological barrier comprising:

a plurality of microneedles each having a base end and a tip;

a substrate to which the base ends of the microneedles are attached or integrated; and wherein the microneedles comprise:

a shell, comprising:

a first poly(vinyl alcohol) (PVA) polymer crosslinked with a first peroxide-sensitive linker; and a peroxide scavenging enzyme encapsulated within a first nanogel, wherein the first nanogel is embedded in the first PVA polymer;

and a core, comprising:

a second poly(vinyl alcohol) (PVA) polymer cross-linked with a second peroxide-sensitive linker;

a glucose-responsive agent encapsulated within a second nanogel, wherein the second nanogel is embedded in the second PVA polymer; and a therapeutic agent, wherein the therapeutic agent is covalently attached to the second PVA polymer with a third peroxide-sensitive linker.

In addition to a therapeutic agent such as insulin, the agent to be delivered to the recipient can also be a prophylactic agent or diagnostic agent. For example, the agent can be selected from the group consisting of peptides, proteins, carbohydrates, nucleic acid molecules, lipids, organic molecules, biologically active inorganic molecules, and combinations thereof. For example, a wide range of drugs may be formulated for delivery with the present microneedle devices and methods. As used herein, the terms "drug" or "drug formulation" are used broadly to refer to any prophylactic, therapeutic, or diagnostic agent, or other substance that which may be suitable for introduction to biological tissues, including pharmaceutical excipients and substances for tattooing, cosmetics, and the like. The drug can be a substance having biological activity. The drug formulation may include various forms, such as liquid solutions, gels, solid particles (e.g., microparticles, nanoparticles), or combinations thereof. The drug may comprise small molecules, large (i.e., macro-) molecules, or a combination thereof. In representative, not non-limiting, embodiments, the drug can be selected from among immunologic adjuvants (for example, monophosphoryl lipid A (MPLA), aluminum salt (Alum), CpG oliogodeoxynucleotides (ODN)), amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and viruses. The drug may be selected from suitable proteins, peptides and fragments thereof, which can be naturally occurring, synthesized or recombinantly produced.

The compositions and/or drug formulation may further include one or more pharmaceutically acceptable excipients, including pH modifiers, viscosity modifiers, diluents, etc., which are known in the art.

In one embodiment, the microneedles comprise hyaluronic acid. In addition to hyaluronic acid, the microneedles may also comprise a variety of materials, including metals, ceramics, semiconductors, organics, polymers, composites, or a combination thereof. Typical materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone).

The microneedles should have the mechanical strength to remain intact while being inserted into the biological barrier, while remaining in place for up to a number of days, and while being removed. In some embodiments, the microneedle must remain intact at least long enough for the microneedle to serve its intended purpose (e.g., delivery of the therapeutic agent).

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips.

The microneedles can be oriented perpendicular or at an angle to the substrate. In one embodiment, the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The cross-sectional dimensions can be between about 1 μm and 1000 μm, such that the base can be about 100-500 μm, and the tip can be between 1 and 20 μm. In one embodiment, the microneedle can be approximately 300 μm at the base, and approximately 5 μm at the tip.

The length of the microneedles typically is between about 10 μm and 1 mm, preferably between 400 μm and 1 mm. In one embodiment, the length (or height) of the microneedle is about 600 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In one embodiment, the microneedles are arranged in a 15 by 15 array with 600 μm tip-to-tip spacing. In one embodiment, the microneedles are arranged in a 20 by 20 array with 600 μtm tip-to-tip spacing.

The shell of the microneedle can be considered as the outside portion of the microneedle that comes into contact with the subject. The core or the microneedle can be considered as the portion of the microneedle located toward the center of each microneedle and is separated from contacting the subject's skin by the shell portion of the microneedle.

In one embodiment, the glucose-responsive agent is glucose oxidase (GOx). Glucose oxidase converts blood glucose to gluconic acid. This leads to production of a peroxide (hydrogen peroxide), and a decrease in the pH.

Methods of Treatment

In some aspects, disclosed herein is a method of delivering a therapeutic agent to a subject, comprising:

administering to a subject in need thereof a microneedle patch, wherein the microneedle patch comprises:

a plurality of microneedles each having a base end and a tip; and a substrate to which the base ends of the microneedles are attached;

wherein the microneedles comprise:

a shell, comprising:

a first poly(vinyl alcohol) (PVA) polymer cross-linked with a first peroxide-sensitive linker; and a peroxide scavenging enzyme encapsulated within a first nanogel, wherein the first nanogel is embedded in the first PVA polymer;

and core, comprising:

a second poly(vinyl alcohol) (PVA) polymer cross-linked with a second peroxide-sensitive linker;

a glucose-responsive agent encapsulated within a second nanogel, wherein the second nanogel is embedded in the second PVA polymer; and a therapeutic agent, wherein the therapeutic agent is covalently attached to the second PVA polymer with a third peroxide-sensitive linker;

and releasing the therapeutic agent from the microneedle patch in the presence of hyperglycemic levels of glucose.

In some aspects, also disclosed herein is a method for treating a disease in a subject in need thereof, comprising:

providing a microneedle patch to a subject, wherein the microneedle patch comprises:

a plurality of microneedles each having a base end and a tip; and a substrate to which the base ends of the microneedles are attached;

wherein the microneedles comprise:

a shell, comprising:

a first poly(vinyl alcohol) (PVA) polymer cross-linked with a first peroxide-sensitive linker; and a peroxide scavenging enzyme encapsulated within a first nanogel, wherein the first nanogel is embedded in the first PVA polymer;

and a core, comprising:

a second poly(vinyl alcohol) (PVA) polymer cross-linked with a second peroxide-sensitive linker;

a glucose-responsive agent encapsulated within a second nanogel, wherein the second nanogel is embedded in the second PVA polymer; and a therapeutic agent, wherein the therapeutic agent is covalently attached to the second PVA polymer with a third peroxide-sensitive linker.

In some embodiments, the method further comprises releasing the therapeutic agent from 30 the microneedle patch in the presence of hyperglycemic levels of glucose.

As used herein, "hyperglycemic levels of glucose" refer to concentrations of glucose which cause, or are at risk of causing, clinical hyperglycemia. Strict cutoff values for hyper-, normo-, and hypoglycemia can vary between subjects, particularly between subjects with varying forms or degrees of severity of diabetes. In some embodiments, a hyperglycemic level of glucose comprises greater than 100 mg/dL glucose. In some embodiments, a hyperglycemic level of glucose comprises 125 mg/dL or greater, 150 mg/dL or greater, 175 mg/dL or greater, or 200 mg/dL glucose or greater. Conversely, "normoglycemic levels of glucose" refer to concentrations of glucose which are typical/normal and are not usually known to relate to clinical conditions (or severe clinical conditions) of glycemic imbalance. In some embodiments, a normoglycemic level of glucose comprises from about 70 mg/dL glucose to less than 200 mg/dL glucose. In some embodiments, a normoglycemic level of glucose comprises from about 70 mg/dL glucose to about 175 mg/dL glucose, from about 70 mg/dL glucose to about 150 mg/dL glucose, from about 70 mg/dL glucose to about 125 mg/dL glucose, or from about 70 mg/dL glucose to about 100 mg/dL glucose. A "hypoglycemic level of glucose" refers to a concentration of glucose which causes, or is at risk of causing, clinical hypoglycemia. In some embodiments, a hypoglycemic level of glucose comprises 70 mg/dL glucose or less. In some embodiments, a hypoglycemic level of glucose comprises 60 mg/dL or less, 50 mg/dL or less, 40 mg/dL or less, or 30 mg/dL glucose or less. In some embodiments, a hyperglycemic level of glucose comprises 200 mg/dL or more glucose, a normoglycemic level of glucose comprises from about 70 mg/dL glucose to less than 200 mg/dL glucose, and a hypoglycemic level of glucose comprises less than about 70 mg/dL glucose.

In some embodiments, the subject has hyperglycemia. In some embodiments, the subject has diabetes or some other glucose regulation disease. In some embodiments, the subject has diabetes. In some embodiments, the subject has Type I diabetes. In some embodiments, the subject has Type II diabetes.

In some embodiments, the glucose-responsive agent produces a peroxide when exposed to hyperglycemic levels of glucose. In some embodiments, the method further comprises detaching the first peroxide-sensitive linker from the first PVA polymer upon exposure to the peroxide.

In some embodiments, the method further comprises detaching the third peroxide-sensitive linker from the second PVA polymer upon exposure to the peroxide. In some embodiments, the detaching of the third peroxide-sensitive linker from the second PVA polymer releases the therapeutic agent from the microneedle patch.

In some embodiments, the method further comprises reducing blood glucose levels. In some embodiments, the blood glucose levels are reduced to no lower than normoglycemic levels. In some embodiments, the therapeutic agent comprises insulin. In some embodiments, the method further comprises terminating release of the therapeutic agent prior to causing hypoglycemia.

In some embodiments, the disease is diabetes. In some embodiments, the disease is Type I diabetes. In some embodiments, the disease is Type II diabetes.

In some embodiments, the first peroxide-sensitive linker comprises a boronic ester. In some embodiments, the first peroxide-sensitive linker detaches from the first PVA polymer upon exposure to peroxide. In some embodiments, the first peroxide-sensitive linker is N1-(4-boronobenzyl)-N3-(4-boronophenyl)-N1,N1,N3,N3-tetramethylpropane-1,3-diaminium (TSPBA).

In some embodiments, the second peroxide-sensitive linker comprises a boronic ester. In some embodiments, the second peroxide-sensitive linker detaches from the second PVA polymer upon exposure to peroxide. In some embodiments, the second peroxide-sensitive linker is N1-(4-boronobenzyl)-N3-(4-boronophenyl)-N1,N1,N3,N3-tetramethylpropane-1,3-diaminium (TSPBA).

In some embodiments, the third peroxide-sensitive linker comprises a boronic ester. In some embodiments, the third peroxide-sensitive linker detaches from the second PVA polymer upon exposure to peroxide. In some embodiments, the third peroxide-sensitive linker is 4-nitrophenyl-(4,4,5,5-tetramethyl-1,3,2-dioxaborolan-2-yl)benzyl carbonate (NBC).

In some embodiments, the glucose-responsive agent comprises glucose oxidase. In some embodiments, the peroxide scavenging enzyme is catalase. In some embodiments, the therapeutic agent is insulin. In some embodiments, the microneedles further comprise hyaluronic acid (HA).

In further aspects, also disclosed herein is a method for treating a disease in a subject in need thereof, comprising:

providing a microneedle patch to a subject, wherein the microneedle patch comprises:

a plurality of microneedles each having a base end and a tip; and a substrate to which the base ends of the microneedles are attached;

wherein the microneedles comprise:

a shell, comprising:

a first poly(vinyl alcohol) (PVA) polymer cross-linked with a first peroxide-sensitive linker; and a peroxide scavenging enzyme encapsulated within a first nanogel, wherein the first nanogel is embedded in the first PVA polymer;

and a core, comprising:

a second poly(vinyl alcohol) (PVA) polymer cross-linked with a second peroxide-sensitive linker;

a glucose-responsive agent encapsulated within a second nanogel, wherein the second nanogel is embedded in the second PVA polymer; and a therapeutic agent, wherein the therapeutic agent is covalently attached to the second PVA polymer with a third peroxide-sensitive linker; and inserting the microneedles into a biological barrier, wherein the presence of hyperglycemic levels of glucose releases the therapeutic agent from the microneedle patch.

In another aspect, disclosed herein is a method for treating hyperglycemia in a subject in need thereof, comprising administering to the subject the microneedle patch of preceding aspect or embodiment. In some embodiments, the hyperglycemia is a symptom of diabetes.

Due to the innovative design with quick responsiveness to a hyperglycemic state, the core-shell patch is able to effectively control blood glucose levels in a normal range. Moreover, the disclosed microneedle patch can avoid the risk of hypoglycemia compared to the native insulin. Current glucose oxidase (GOx)-based glucose-responsive insulin delivery systems mainly utilize matrices consisting of pH-sensitive materials, the response speed of which is extremely slow (as it is hard to reduce pH level efficiently in a physiologically buffered system) and therefore remain challenging for clinical translation. In the present disclosure, enzymatically generated $H_2O_2$ is directly applied as a trigger for self-regulating insulin release, based on both dissociation of matrix and detachment of insulin. This leads to a remarkably faster and sharper responsiveness upon glucose level changes in both in vitro and in vivo studies.

The microneedle patches disclosed herein also have excellent biocompatibility. In some embodiments, the base of the microneedle patches and the matrix of microneedles were made from hyaluronic acid (HA) and poly (vinyl alcohol) (PVA) respectively, which are highly biocompatible and can be further tailored. Both HA and PVA have been widely applied in numerous FDA-approved therapeutic formulations or medical devices due to excellent biocompatibility and biodegradability. In addition, previously applied hypoxia-responsive systems to enhance the response speed caused severe inflammation for long-term usage due to $H_2O_2$. In the present disclosure, the excessive $H_2O_2$ generated by oxidation of glucose was restricted within the space of microneedle by a surface coated membrane, which can protect normal tissues from the damage of $H_2O_2$.

The microneedle patches disclosed herein also can be conveniently administered. Integration of the crosslinked gel with a microneedle array patch provides a painless and disposable administration modality. Additionally, the insulin dose and response speed can be readily adjusted upon personalized requirement. This platform is also much more convenient compared to an insulin pump with implanted needles/electrodes or other needle-injection systems.

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Core-Shell Microneedle Gel for Self-Regulated Insulin Delivery

Results

Figure 7A:
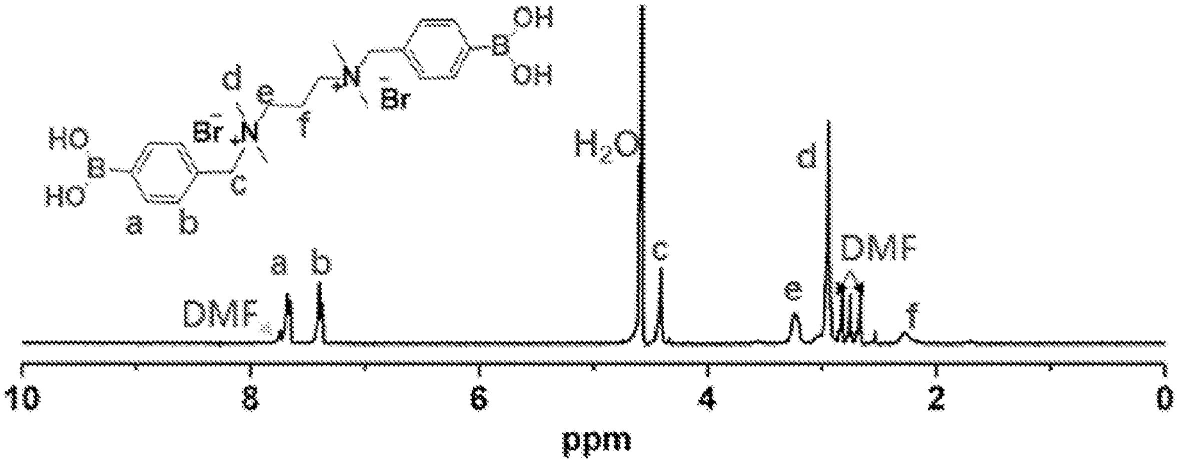
FIGS. 7A-7B. H1-NMR (300 MHz, in D2O) of TSPBA before and after oxidization in PBS.
Figure 7B:
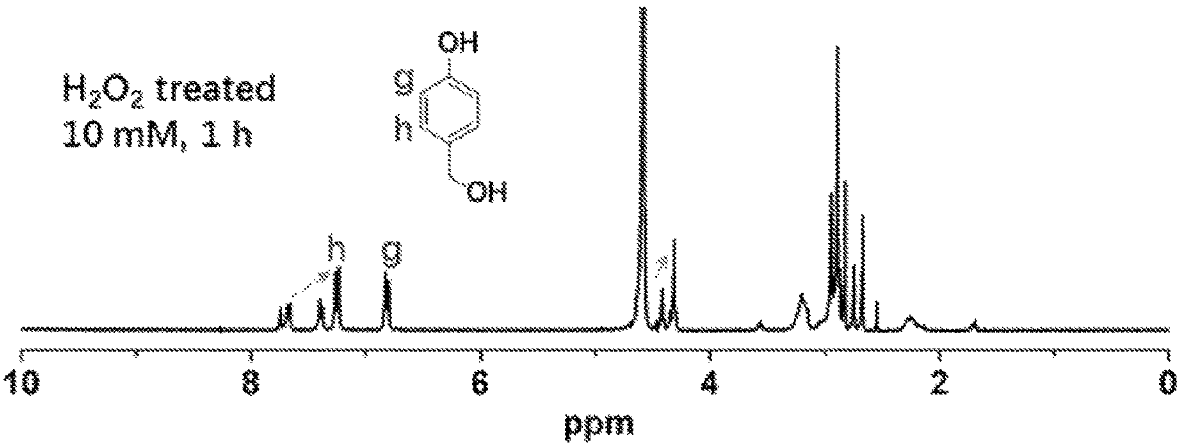
Figure 8:
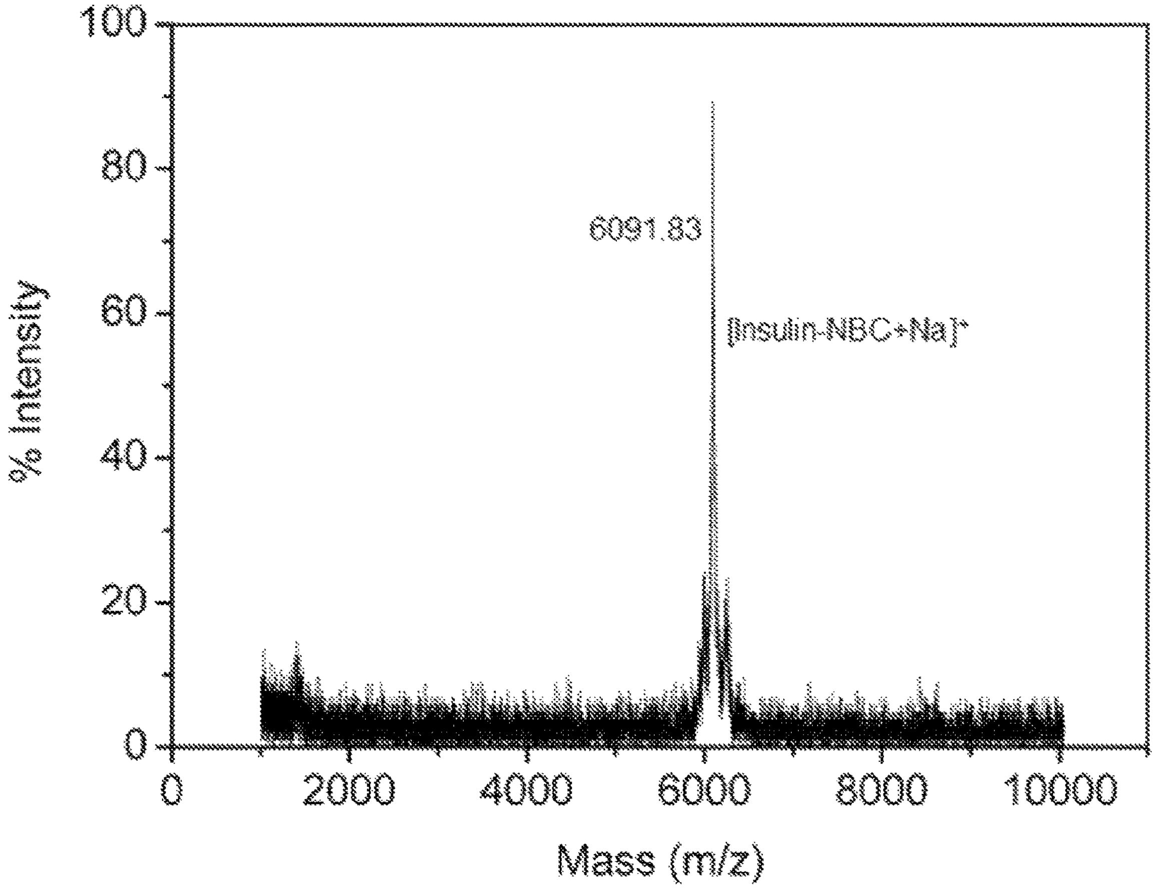
FIG. 8. MALDI-TOF mass spectrum of the purified insulin-NBC.
Figure 9A:
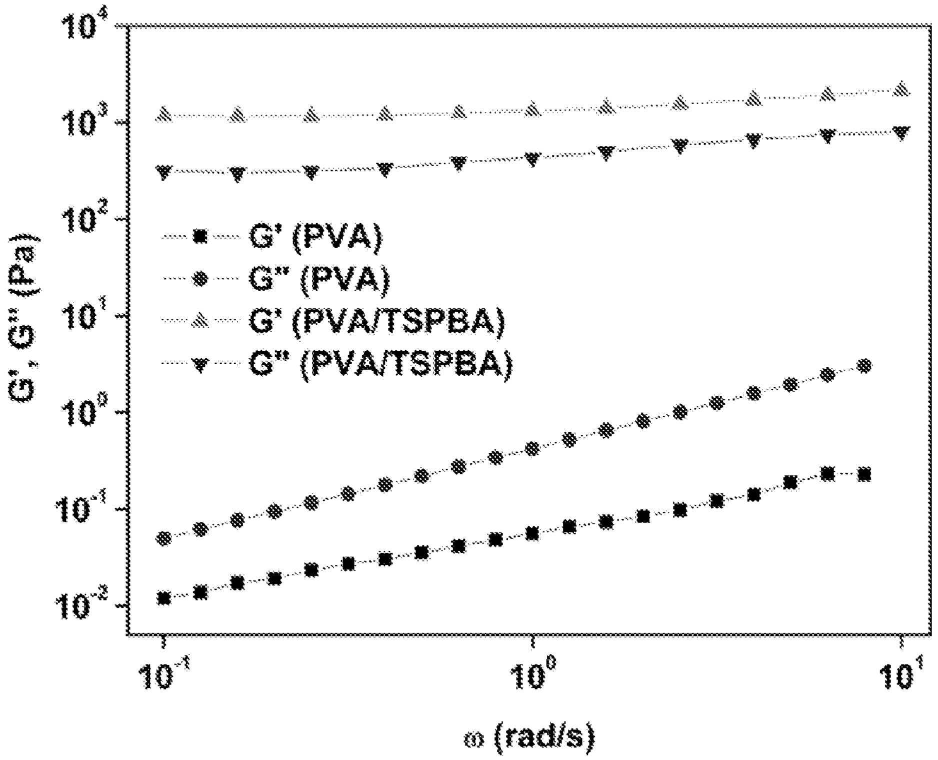
FIGS. 9A-9B. Dynamic rheological behavior of PVA before and after gelation at 25° C. measured using a TA Instruments AR-2000 stress controlled rheometer with 25 mm aluminum cross-hatched parallel plates. All experiments were conducted in the linear viscoelastic regime with a 500 μm gap between the plates.
Figure 9B:
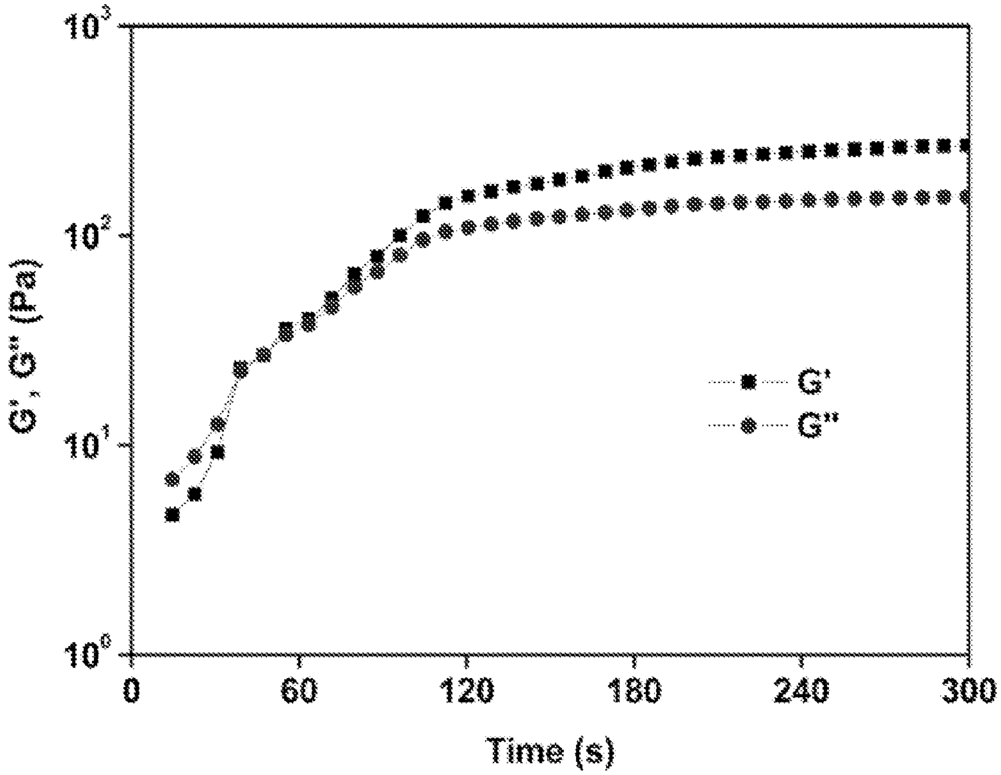

TSPBA was synthesized via quaternization reaction of N1,N1,N3,N3-tetramethylpropane-1,3-diamine with an excess of 4-(bromomethyl)phenylboronic acid (Scheme 1). The quaternary ammonium groups on TSPBA greatly enhanced its water solubility (~100 mg/mL), which facilitating the gel formation with PVA aqueous solution without organic solvents. Upon oxidation in the presence of 10 mM $H_2O_2$, 70% of TSPBA released p-quinone methide (p-hydroxylmethylenephenol) and became tertiary amines in two hours as demonstrated by H1-NMR (FIG. 7).[18] Insulin-NBC was prepared in the presence of a slight excess of NBC in a mixed solvent composed of DMSO and 10 mMNa$HCO_3$ aqueous solution.[19] The product was purified using preparative scale high performance liquid chromatography (HPLC),[13] and was confirmed by molecular weight to be a conjugate of one insulin modified by one NBC by MALDI-TOF mass spectroscopy (FIG. 8). Importantly, insulin-NBC had much higher aqueous solubility (>100 mg/mL) at pH 7.4 than native insulin, which was critical to prepare MN gels with a high loading capacity of insulin. The phenylboronic ester of insulin-NBC can be hydrolyzed in an aqueous solution; this reaction is facilitated in the presence of diols.[19] The insulin-NBC could then be conjugated to PVA chains via the kinetic ester bond between the phenylboronic acid and the cis-1,3-diols in PVA.[21] Addition of TSPBA to this reaction solution led to a rapid increase in the elastic (G') modulus and formation of a network between the PVA chains in 60 s (FIG. 9).[22] The gelation of PVA by TSPBA is critical for maintaining the integrity of the shell structure, which is composed of water-sensitive materials, and specifically prevents its dissolution to aqueous solution when preparing the core.

Scheme 1

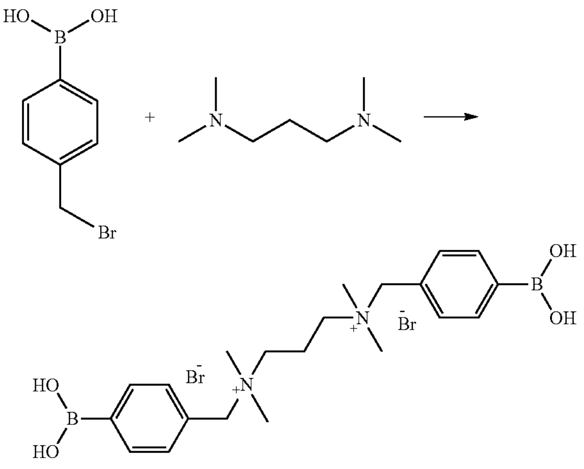

TSPBA

Figure 2A:
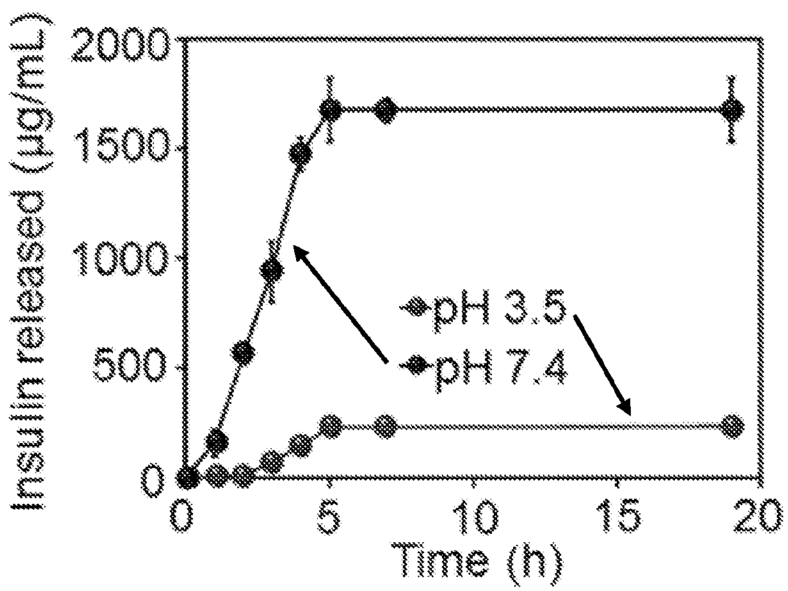
FIGS. 2A-2F. In vitro glucose-responsive insulin release from PVA-TSPBA gels.

The $H_2O_2$-sensitive insulin release was evaluated in the presence of 10 mM $H_2O_2$ in PBS at pH 7.4. Insulin was released from a formed gel with the addition of $H_2O_2$ at a steady rate, and more than half of insulin was released within two hours (FIG. 2*a*). Although the esters between phenylboronic acids and diols are unstable in acidic solution,[23] the gel formed between PVA and phenylboronic acid is stable in acidic environment.[21] At pH 3.5, the gel showed high stability and insulin was released at a rather slow rate as compared to pH 7.4.

Figure 2B:
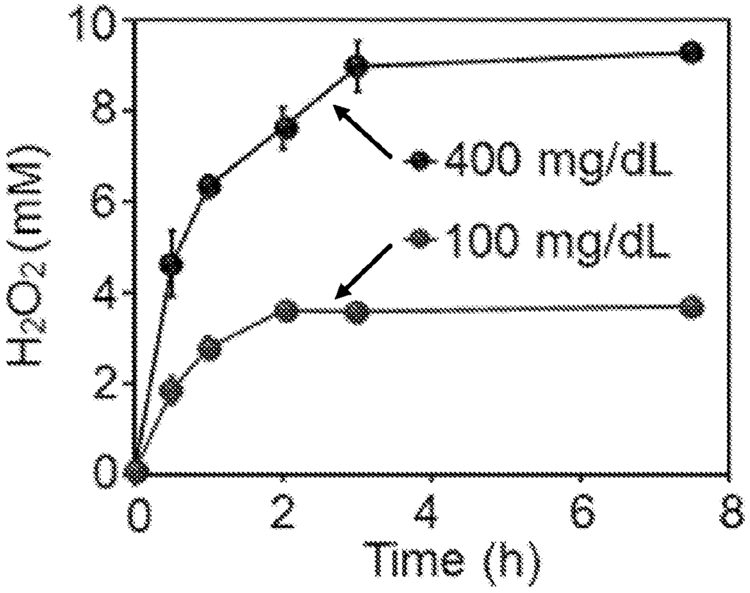
Figure 2C:
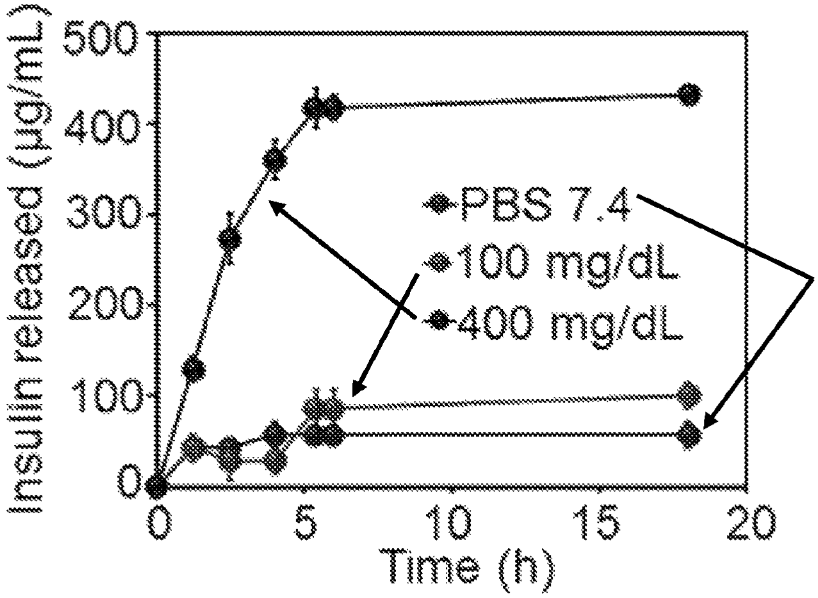
Figure 2D:
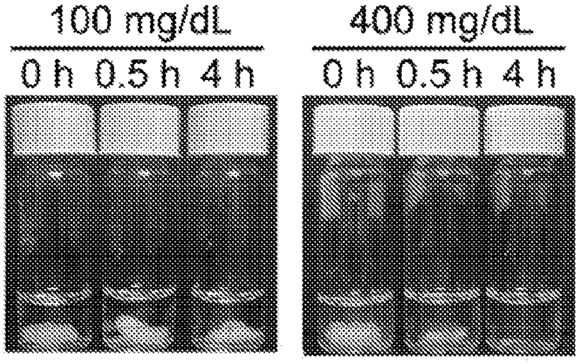

Next, the release rate of insulin was assessed in the presence of GOx in PBS at initial pH 7.4 at 3 different glucose concentrations, including a typical hyperglycemic level (400 mg/dL), a normoglycemic level (100 mg/dL), and a control level (0 mg/dL). The $H_2O_2$ generation rate was measured using a fluorometric hydrogen peroxide assay kit.[24] At the hyperglycemic glucose concentration of 400 mg/dL, $H_2O_2$ generation was efficient and reached as high as 6 mM within 30 min (FIG. 2*b*). Compared to the hyperglycemic solution, $H_2O_2$ was generated at a much slower rate in the normoglycemic solution of 100 mg/dL glucose. The insulin release corresponded to the $H_2O_2$ release such that the insulin release rate was dramatically promoted under a glucose concentration of 400 mg/dL compared to that of 100 mg/dL, whereas negligible insulin release was observed when the gel was incubated in the control solution (FIG. 2*c*), consistent with the morphology change of gels (FIG. 2*d*).

Figure 2E:
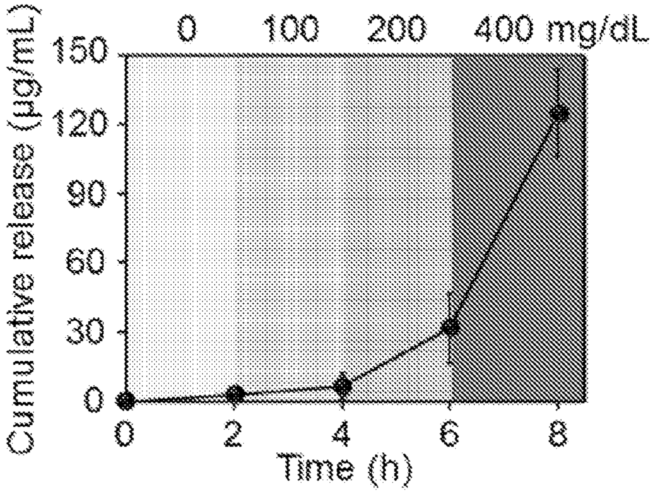
Figure 2F:
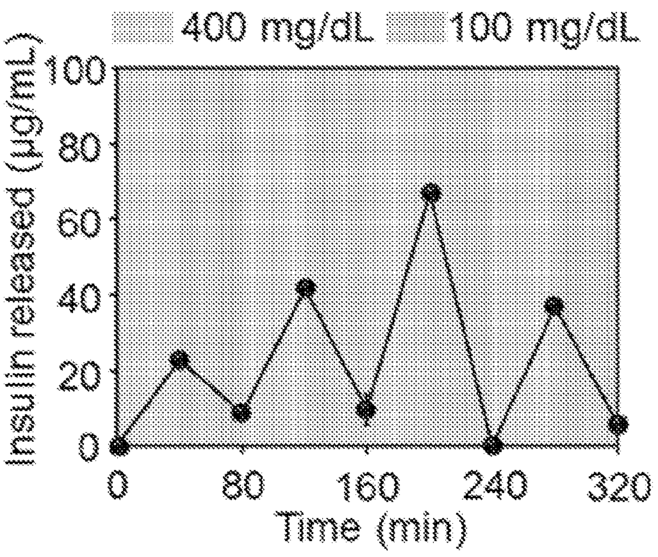
Figure 10:
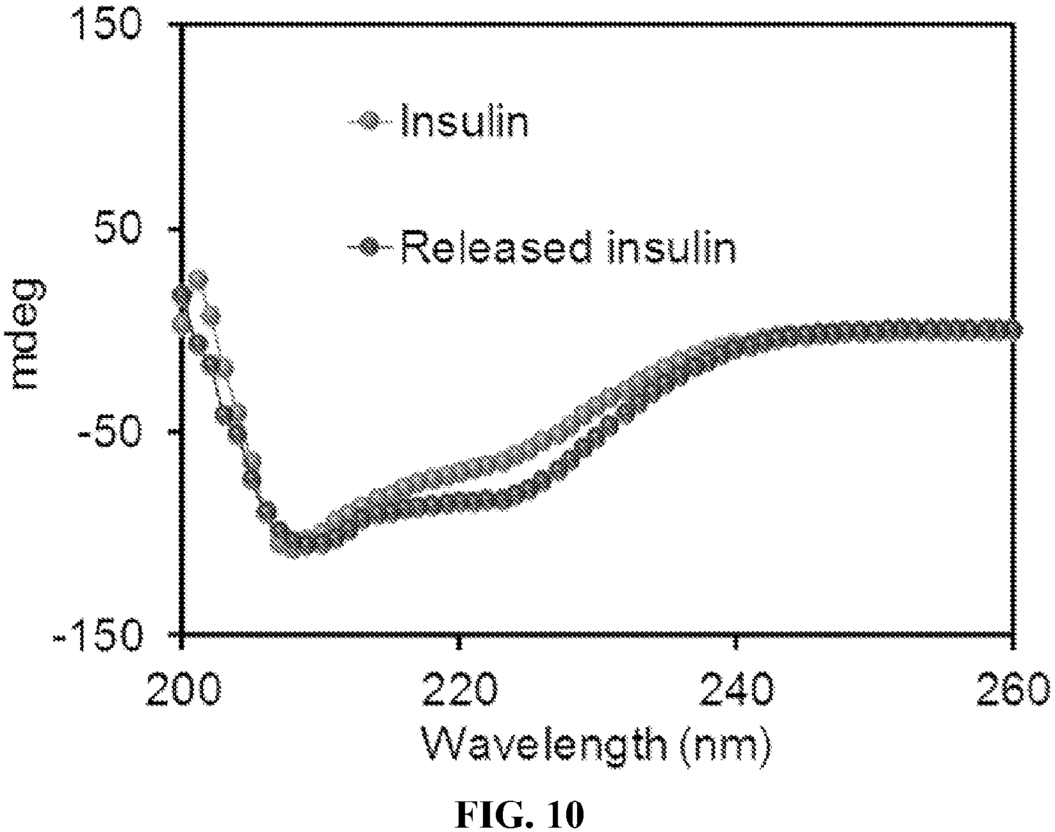
FIG. 10. CD spectra of native insulin solution and insulin released from the gels incubated with 400 mg/dL glucose.

Moreover, the release rate of insulin from PVA-TSPBA gels was steadily enhanced when gradually increasing the glucose concentrations of the tested solutions from normoglycemic to hyperglycemic conditions, where a maximum of a 15-fold difference in insulin release rate was achieved in two hours when the glucose concentration was increased from 100 to 400 mg/dL (FIG. 2*e*). The limited release of insulin at normoglycemia is a significant safety feature for the in vivo application. Additionally, a pulsatile kinetic release profile of insulin was monitored for several cycles by alternately varying glucose concentrations between normoglycemic and hyperglycemic conditions, and the pulsatile release profile of insulin was achieved when the gels were alternatively exposed to the normal and hyperglycemic levels (FIG. 2*f*). In sum, these findings suggest that the dissociation of crosslinked gels only takes place in hyperglycemic conditions and the PVA-TSPBA gels release insulin in a glucose concentration-dependent behavior. Finally, the far-UV circular dichroism (CD) spectra of the native and released insulin from gels (1 mg/mL) were similar, suggesting that released insulin retains α-helical secondary structure and bioactivity (FIG. 10).

Figure 3A:
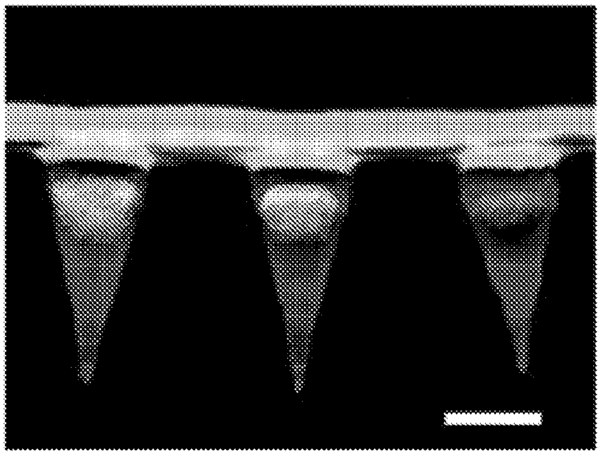
FIGS. 3A-3G. Characterization of a microneedle (MN) array patch of PVA-TSPBA.
Figure 3B:
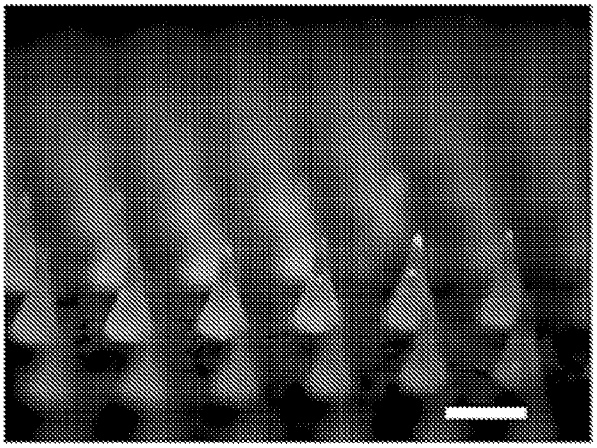
Figure 3C:
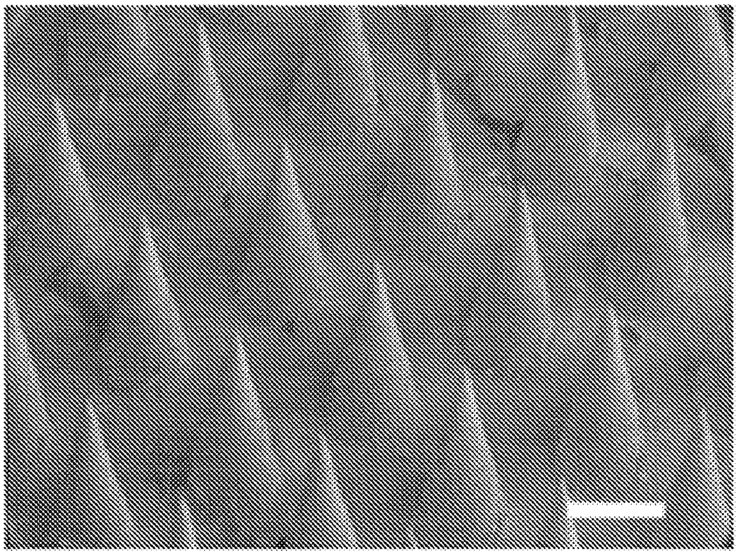
Figure 3D:
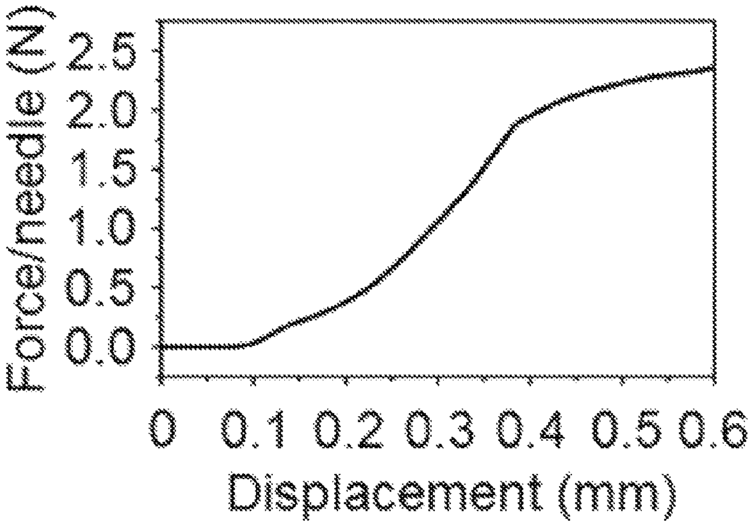
Figure 3E:
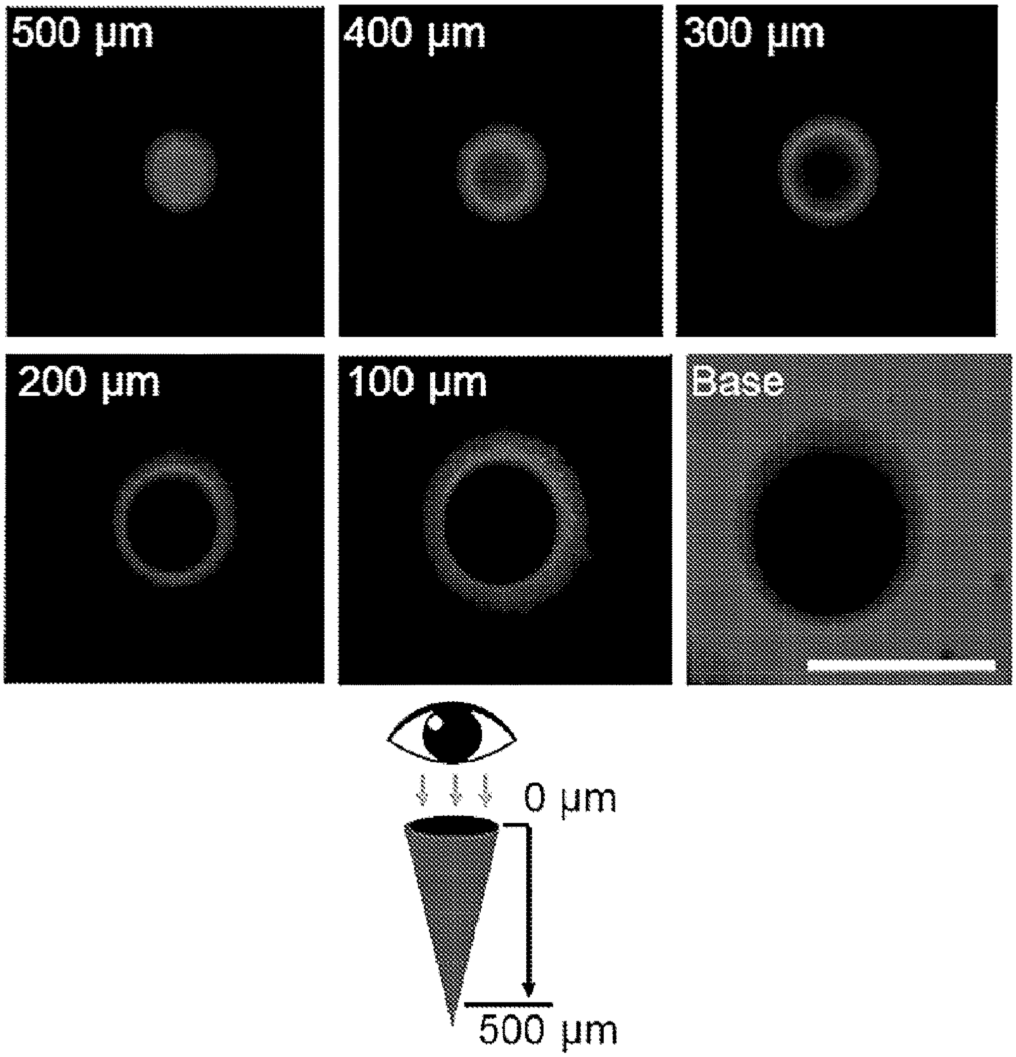
Figure 3F:
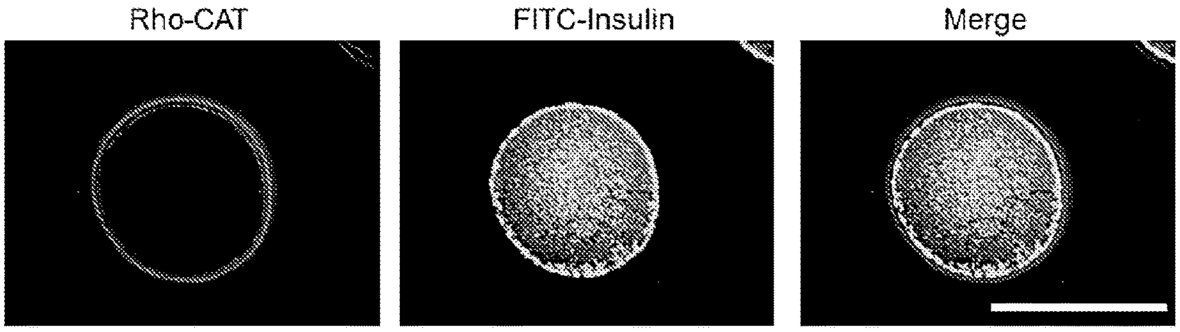
Figure 3G:
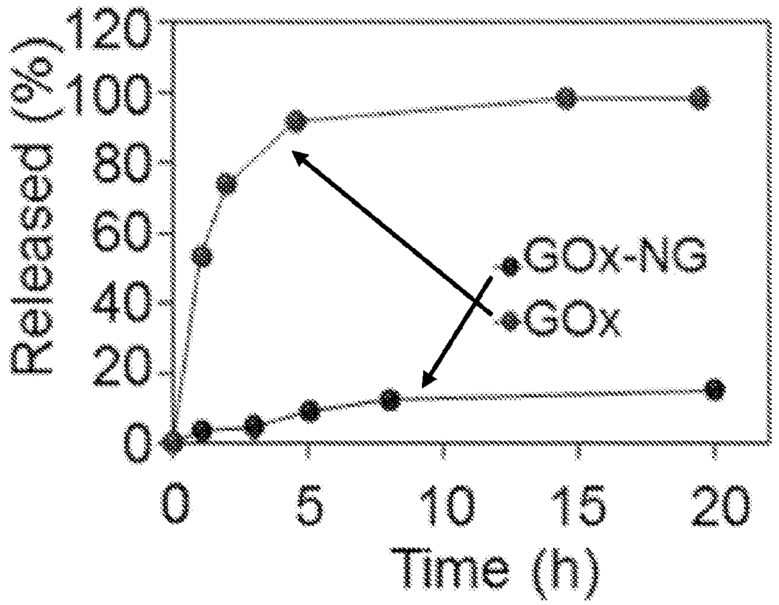
Figure 11A:
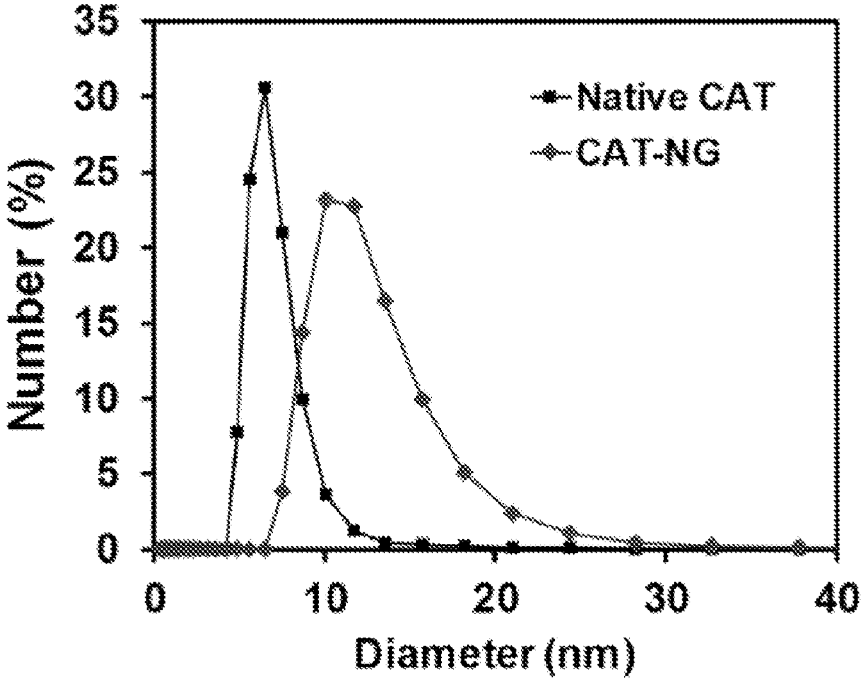
FIGS. 11A-11B. Characterization of CAT-NG.
Figure 11B:
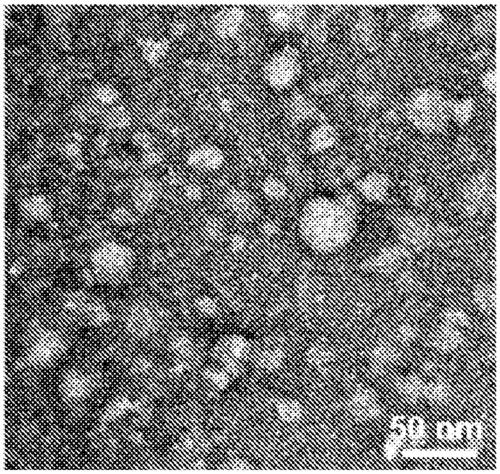
Figure 12A:
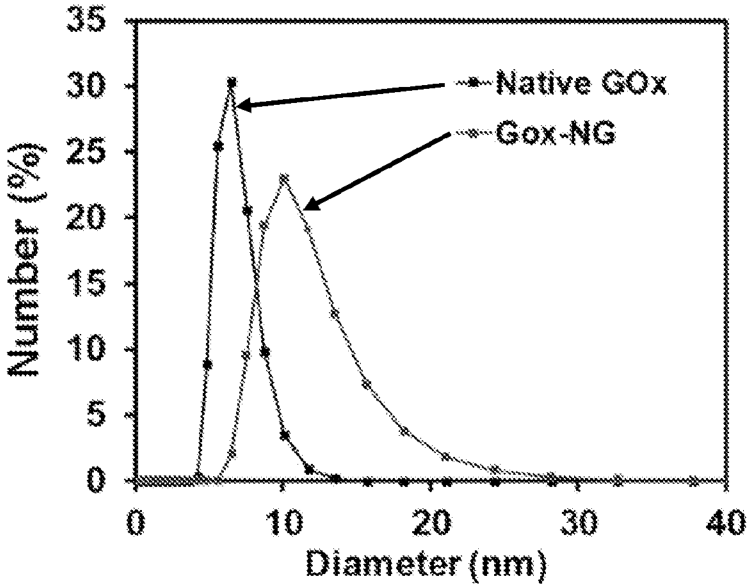
FIGS. 12A-12B. Characterization of GOx-NG.
Figure 12B:
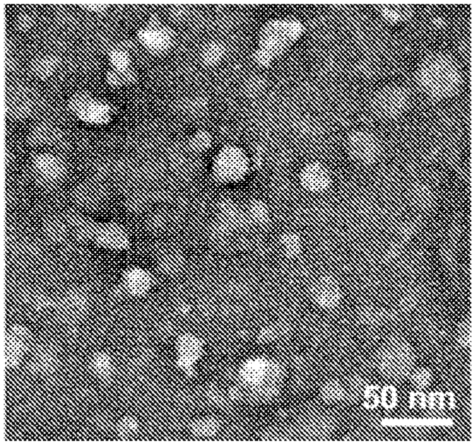
Figure 13A:
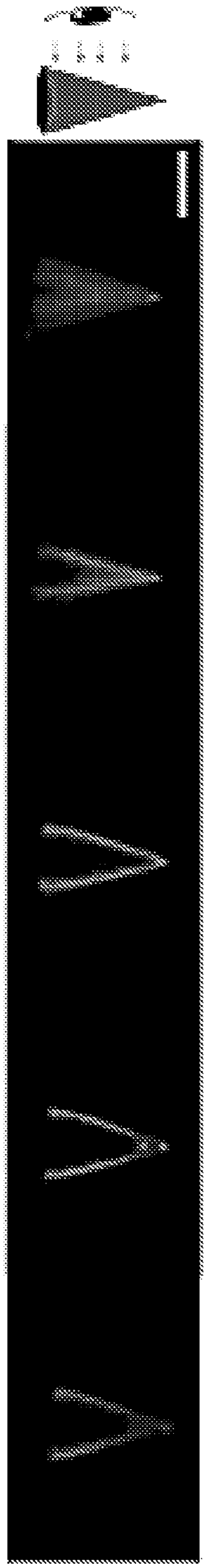
FIGS. 13A-13B. Representative images of hollow CAT loaded MNs: side view (FIG. 13A) and overhead view (FIG. 13B). The intervals for b was 80 μm at direction from bottom to top of microneedle.
Figure 13B:
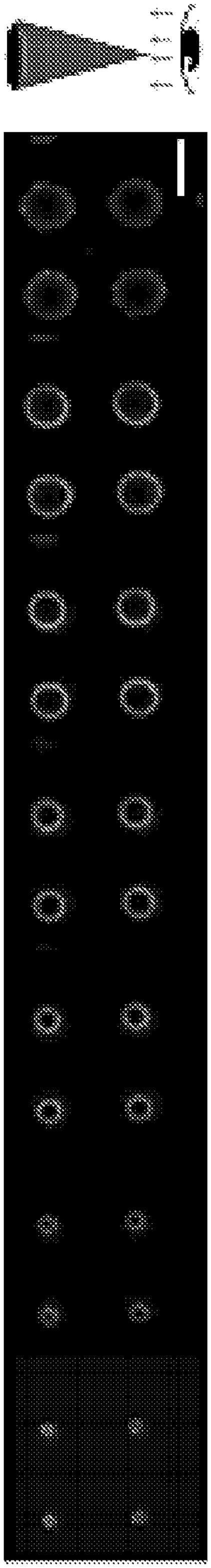
Figure 14:
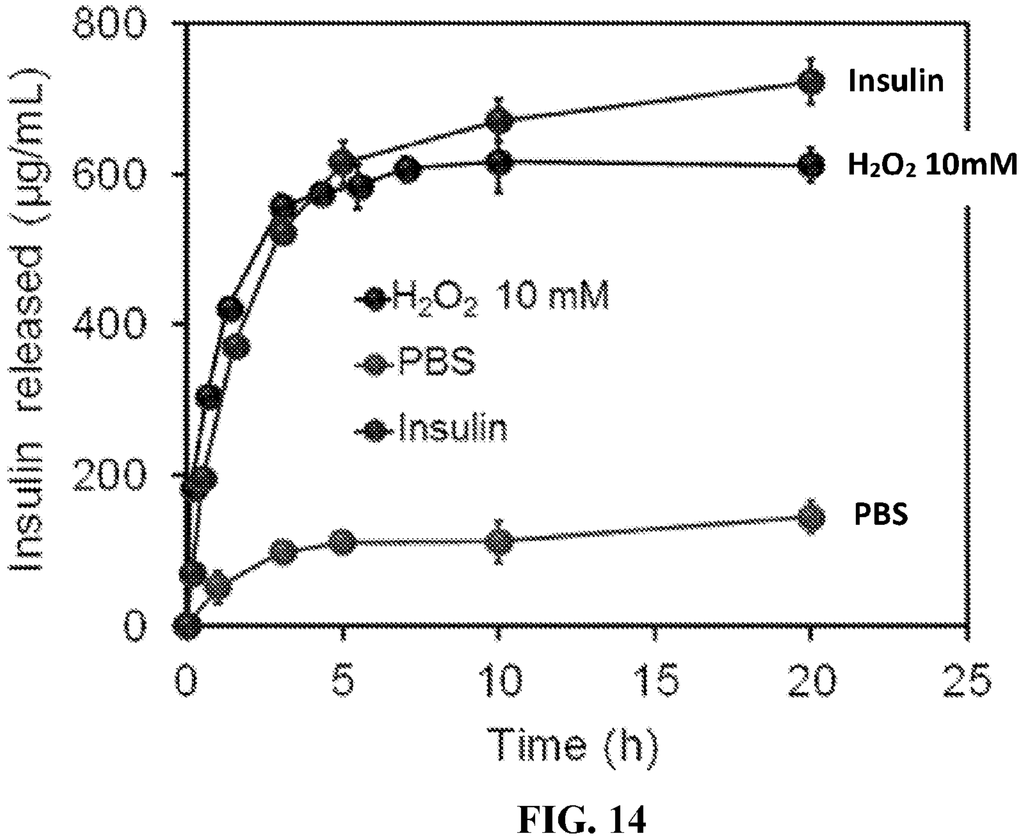
FIG. 14. The $H_2O_2$ dependent release of insulin from insulin-NBC loaded in PVA methacrylate gel. Native insulin was used as control.

To fabricate the core-shell MN gel, PVA-TSPBA gels were integrated into MN array patch using a micromolding approach[9] A "solution-gelation" method was developed to conveniently load the crosslinked gel into MNs and form a core-shell structure. Briefly, diluted aqueous solutions of PVA, TSPBA and CAT-NG (FIG. 11) with low viscosity were prepared, combined, and deposited in a silicone mold. The mixed solution was kept in the mold under vacuum for 30 minutes and then centrifuged at 500 rpm for one hour to form a "shell" on the mold. Another round of diluted aqueous solutions of PVA, TSPBA and GOx-NG (FIG. 12) were loaded into the mold and this procedure was repeated for several times until a predetermined amount of insulin-loaded gel was achieved. During this process, acrylated PVA and radical initiator was added to the native PVA aqueous solution to form a partially non-degradable network. Finally, hyaluronic acid (HA) aqueous solution was cast and dried under vacuum to provide a base for the mechanical support. [9] The resulting device was arranged in a 20×20 MN array on a 10×10 mm2 patch. The needle had a conical shape with a base diameter of 300 μm, 5 μm at the tip, and a height of 600 μm (FIG. 3*a*). The structure of MNs was confirmed with SEM and fluorescence microscopy (FIG. 3*b*, 3*c*). The mechanical strength of MN was determined as 2 N/needle (FIG. 3*d*), which sufficiently allows for skin insertion without breaking.[25] To validate the feasibility of coating a CAT layer on MN arrays, a hollow MN array patch constructed by rhodamine B labeled CAT-NG loaded PVA-TSPBA gel shell was prepared. These hollow MNs showed a complete shell structure in a bottom-view, side view or overhead view (FIGS. 3*e* and 13). In addition, it was found found that the integrity of this CAT-NG-loaded shell was not affected when preparing the core part (FIG. 3*f*). Collectively, these results demonstrated the feasibility of preparing a core-shell MN array, with a core loaded with insulin and GOx-NG, in addition to a shell embedded with CAT-NG. The methacrylated PVA formed gel was shown to selectively release insulin over GOx-NG (FIGS. 3*g* and 14). Release of GOx-NG was likely prevented due to its much larger size (~12 nm) than insulin and the covalent bond, thereby reducing the potential local and systemic toxicity of GOx. [16]

Figure 4A:
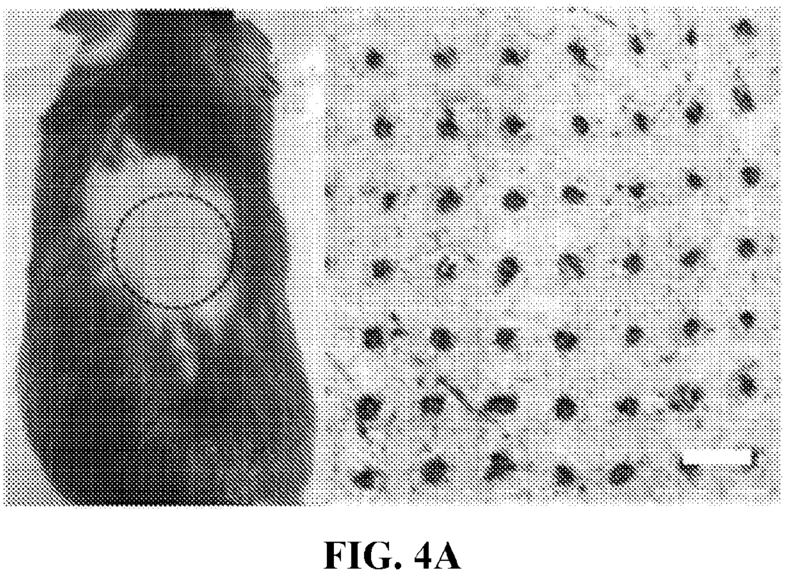
FIGS. 4A-4H. In vivo studies of MN array patches for type 1 diabetes treatment.
Figure 4B:
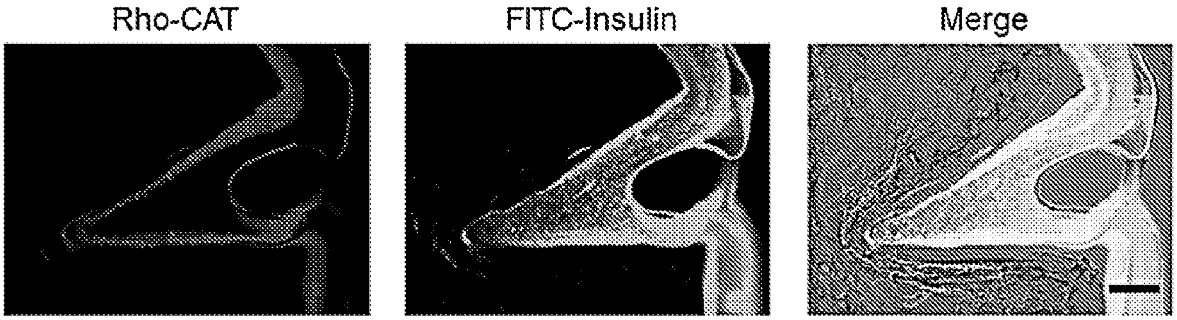
Figure 15:
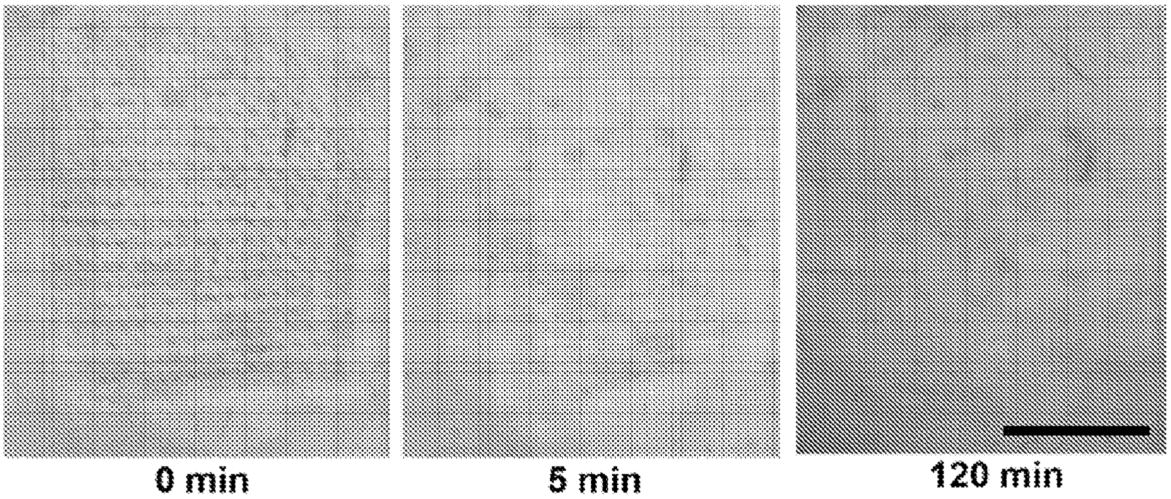
FIG. 15. Skin puncture marks at 0 min, 5 min and 120 min post-treatment of MNs. Scale bar, 0.5 cm.

The in vivo performance of the core-shell MN array patches was evaluated in a mouse model of type 1 diabetes induced by streptozotocin (STZ). The mice were divided into six groups: 1) treatment with CAT-NG shelled MN array patch of GOx-NG and insulin-NBC loaded gels (MN-CAT); 2) treatment with subcutaneous injection of human recombinant insulin; 3) treatment with MN array patch of GOx-NG and insulin-NBC loaded gels (MN-Gel(G+I)) without shell; 4) treatment with only microneedle array patch loaded blank gel (MN-Gel); 5) treatment with an MN array patch of insulin-NBC loaded gels (MN-Gel(I)); 6) group treated by MN array patch of GOx and insulin and CAT-NG loaded gels (MN-Gel(G+C+I)). The insulin dosage was set as 50 mg/kg for all MN based insulin treatments. Staining by trypan blue indicated successful penetration of MNs in excised skin (FIG. 4*a*, *b*).[26] In addition, the temporal microchannels on the skin caused by MNs recovered quickly within two hours post-treatment (FIG. 15, Supporting Information).

Figure 4C:
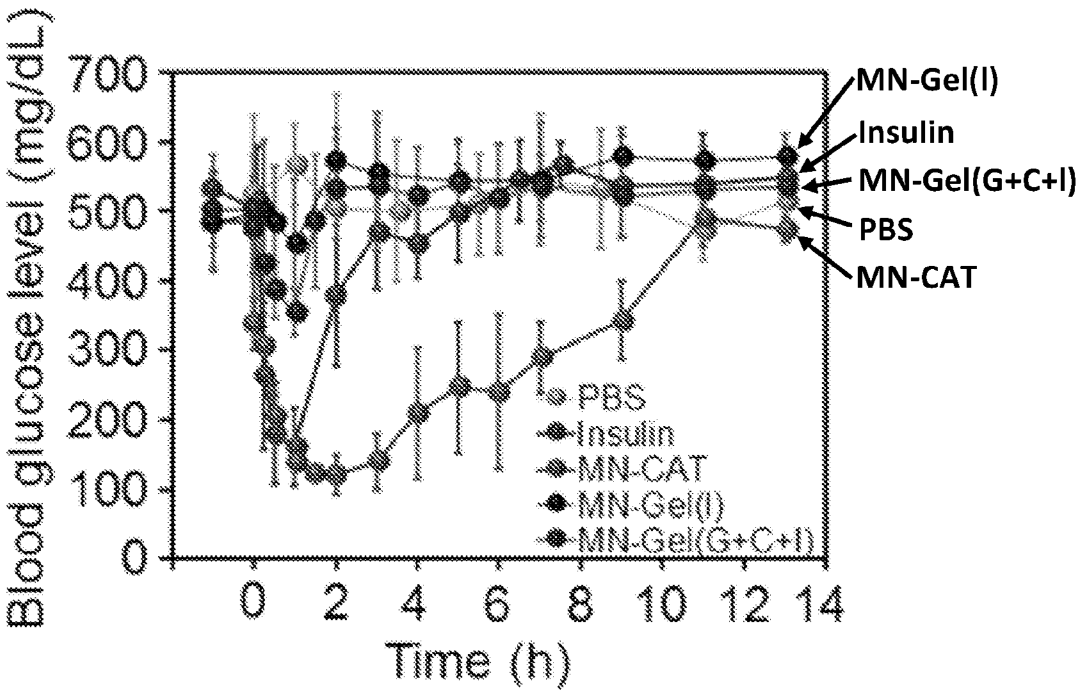
Figure 16:
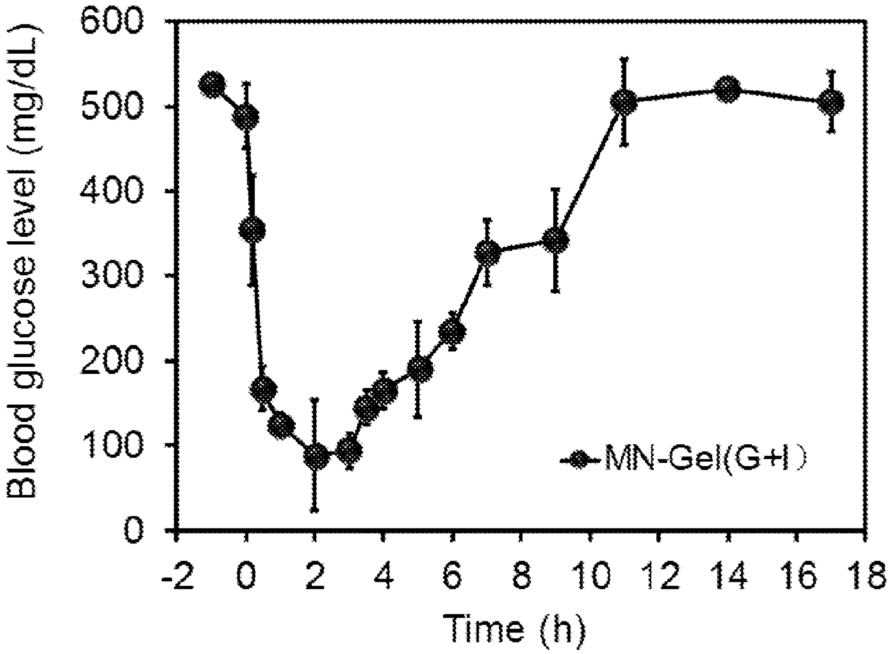
FIG. 16. Blood glucose level of type 1 diabetic mice treated by MN-Gel (G+I).
Figure 17:
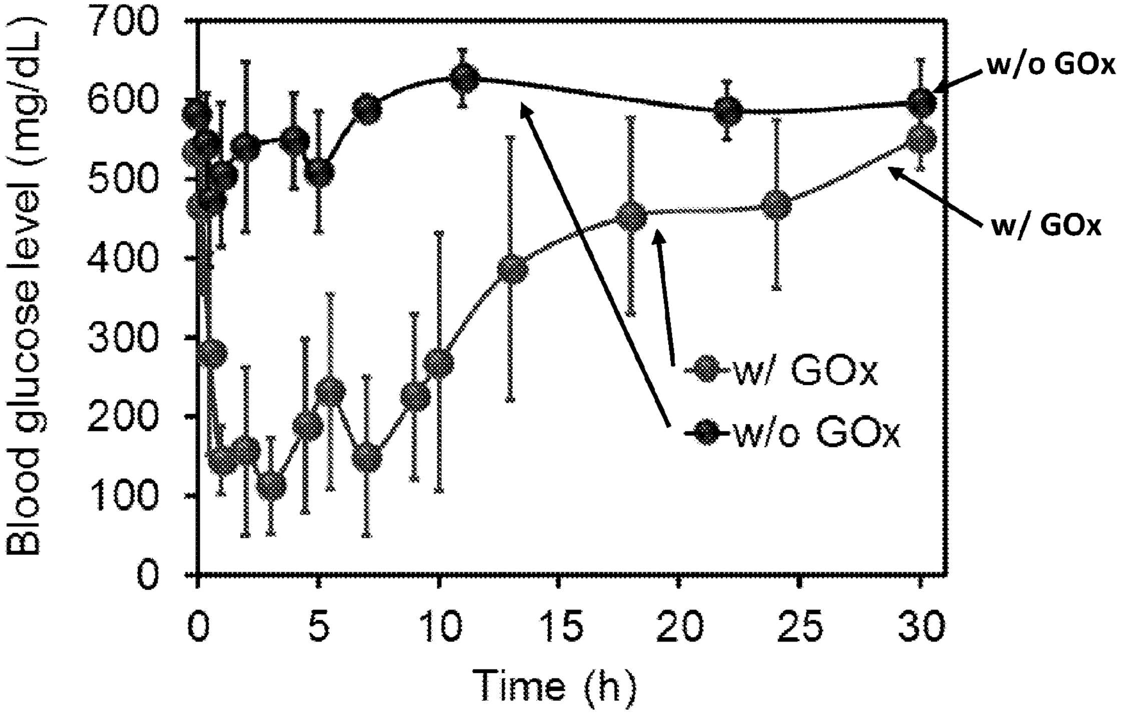
FIG. 17. Blood glucose levels in streptozotocin (STZ)-induced diabetic mice after treatment with insulin-NBC loaded PVA-TSPBA gel with or without GOx.
Figure 18:
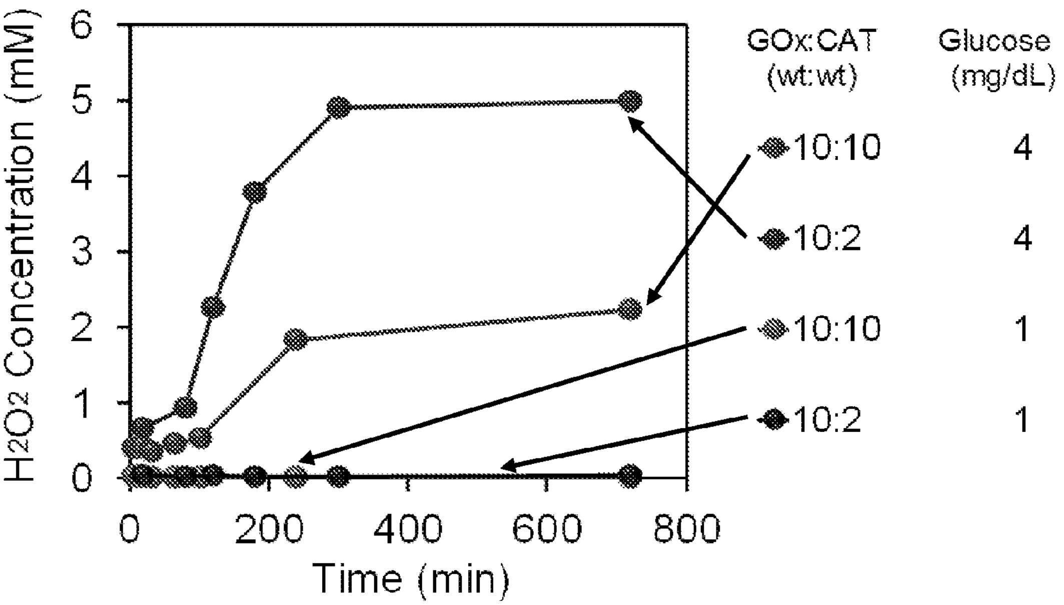
FIG. 18. The $H_2O_2$ generation rate through oxidation of glucose by GOx in the presence of CAT of different ratio in glucose solution (100 or 400 mg/dL) in PBS with an initial pH at 7.4. The concentration of GOx was set as 0.2 mg/mL.
Figure 19:
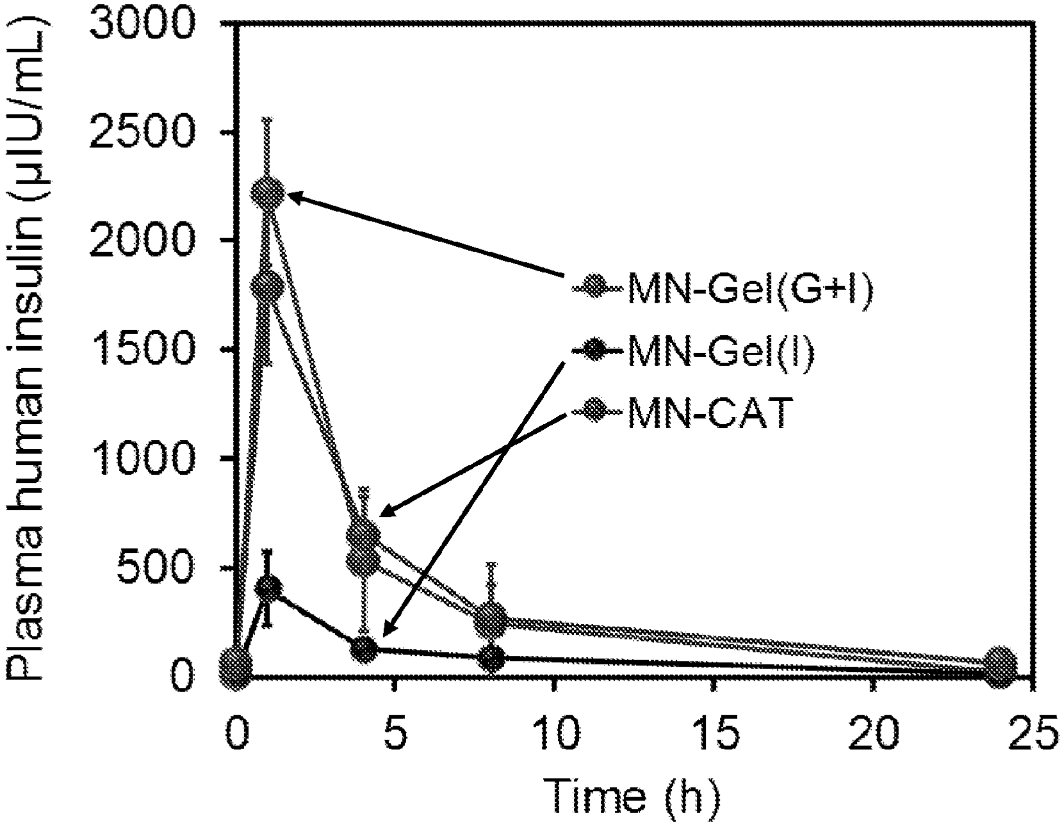
FIG. 19. The plasma human insulin levels in mice treated with MN-CAT, MN-Gel(I), or MN-Gel(G+I).

BGLs of the mice were monitored over time following administration. A rapid decrease of BGLs of mice treated by MN-Gel(G+I) (FIG. 16) and MN-CAT (FIG. 4*c*) was observed in 30 min post-administration, and BGLs then slowly decreased to around 100 mg/dL and maintained near 200 mg/dL for almost six hours, much longer than subcutaneously injected insulin (FIG. 4*c*). This was attributed to the quick local generation of $H_2O_2$ through the oxidation of glucose in the presence of GOx, as well as the high sensitivity of gel to $H_2O_2$. In contrast, no obvious BGLs reduction was observed for the mice treated with MN-Gel(I), MN-Gel (G+C+I) and MN-Gel. These results were consistent to that observed in diabetic mice subcutaneously injected with PVA-TSPBA gel with or without GOx (FIG. 17). Taken together, these observations confirmed the essential role of $H_2O_2$ in releasing insulin, as well as the high stability of insulin in PVA-TSPBA in the physiological environment. In vitro, CAT can preferentially decompose $H_2O_2$ efficiently at normoglycemia (100 mg/dL) (FIG. 18). However, the capability of MN-Gel(G+C+I) to reduce BGLs was significantly limited (FIG. 4*c*), indicating the necessity to separate CAT in a shell layer to establish a robust level of $H_2O_2$ locally. Additionally, the plasma human insulin levels in mice treated with MN-CAT and MN-Gel(G+I) were significantly higher than those treated with MN-Gel(I) (FIG. 19).

Figure 4D:
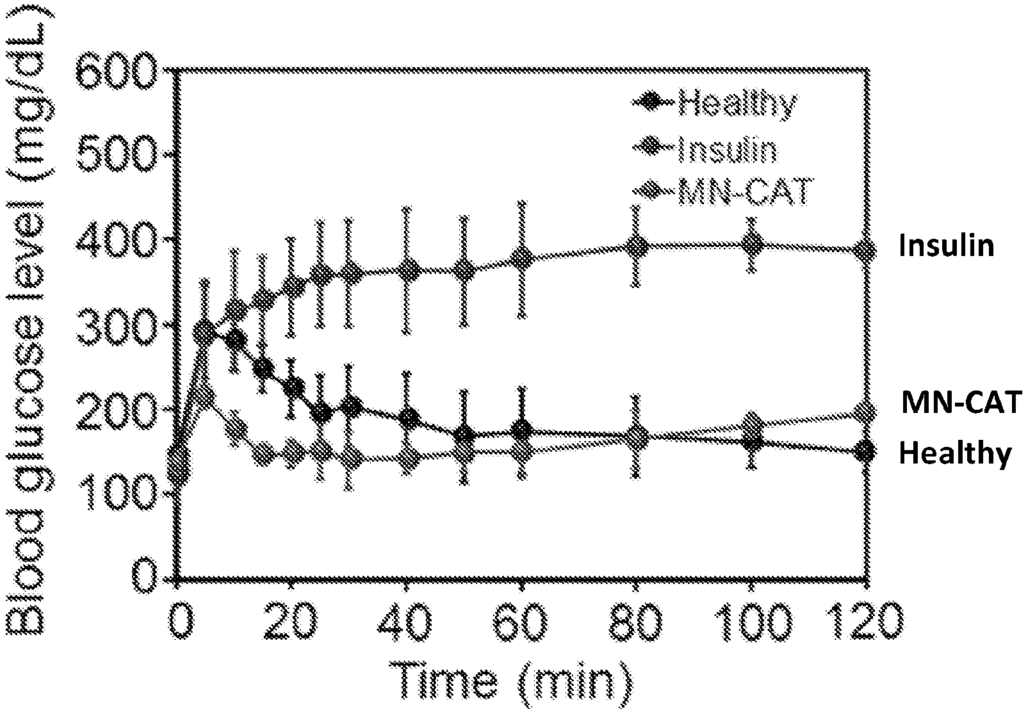
Figure 4E:
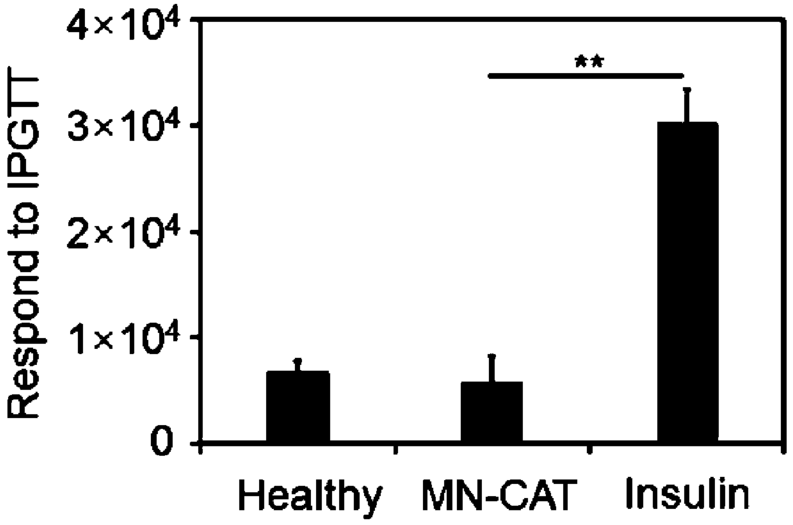
Figure 4F:
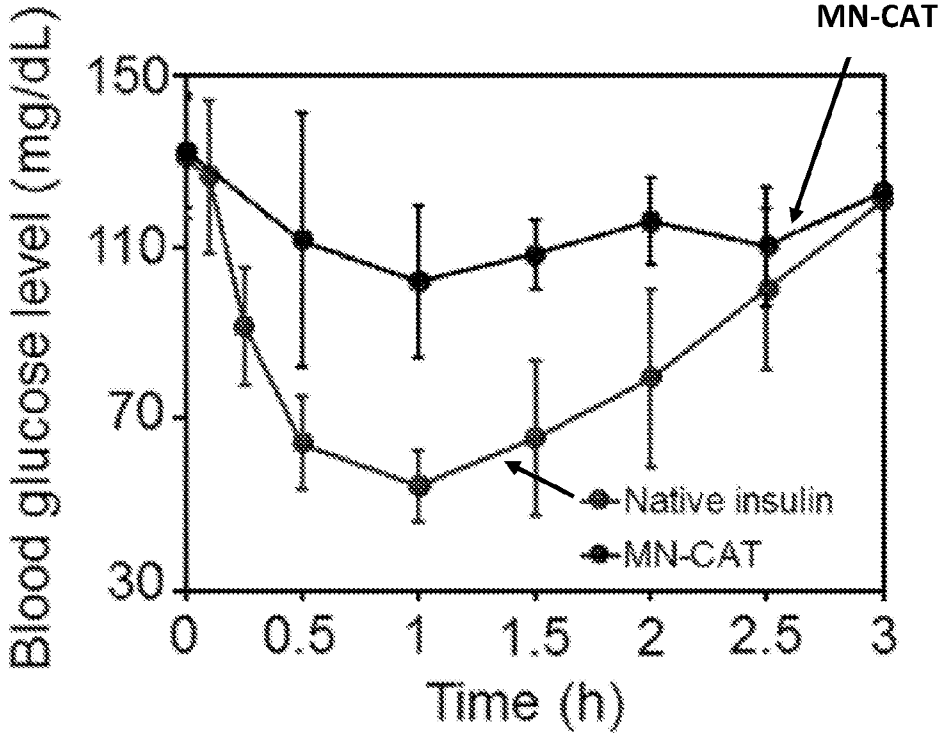
Figure 4G:
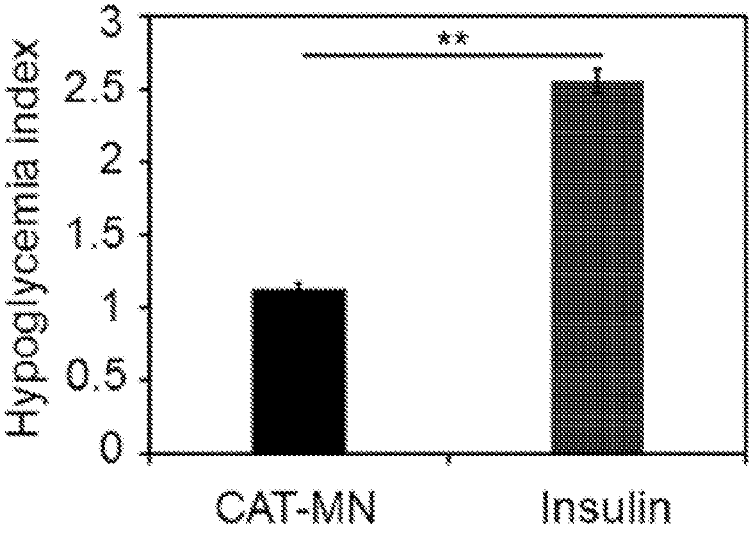
Figure 4H:
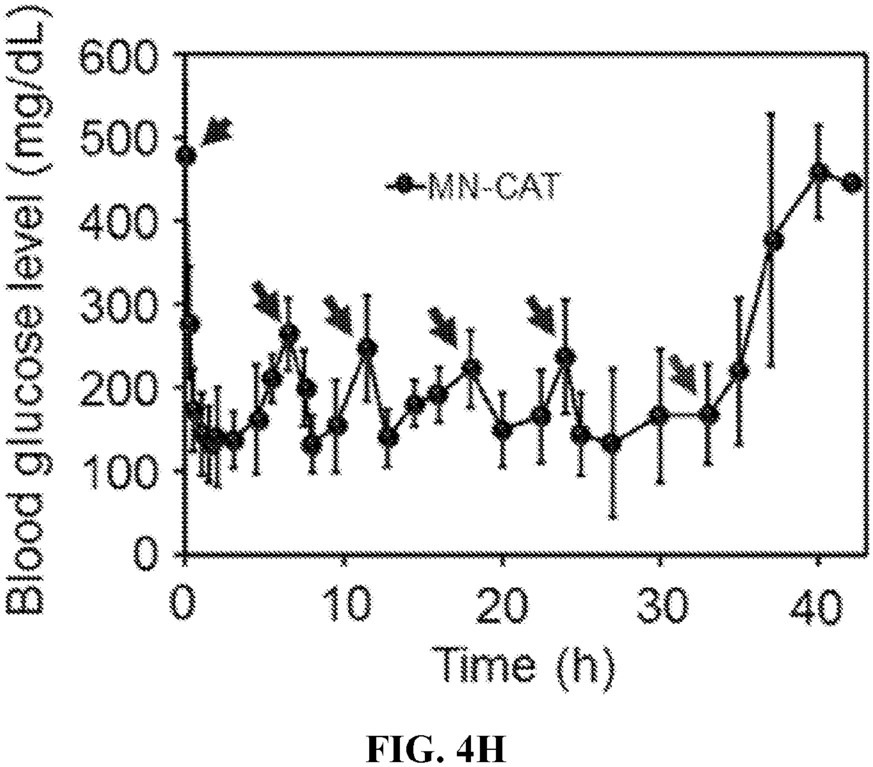

Intraperitoneal glucose tolerance tests (IPGTTs) were further carried out one-hour post-administration of MNs or insulin. A spike in BGLs was observed for all groups after the IPGTT (FIG. 4*d*). However, only healthy mice and MN-CAT could restore blood glucose levels to a normoglycemic level within a short period of time, and the mice treated with MG-CAT showed significantly enhanced glucose tolerance to the glucose challenge (FIG. 4*e*). In order to assess the risk of hypoglycemia associated with treatment by MN-CAT, the BGLs of healthy mice treated with MN array patch were observed. The BGLs of mice treated with insulin showed a remarkable decrease, while the BGLs of mice treated with MN-CAT showed only a slight decrease, consistent with the slow release of insulin from gels at the normoglycemic state (FIG. 4*f*). Additionally, the MN-CAT treated group showed significantly lower hypoglycemia index than insulin (FIG. 4*g*), suggesting that the MN-CAT is safe for clinical application. Furthermore, a 40-hour long consecutive MN administration was performed to evaluate the in vivo glucose control capability of MN (FIG. 4*h*). During this time, BGLs were maintained in a narrow range between 100 to 250 mg/dL, and critically, no hypoglycemia was recorded.

Figure 5A:
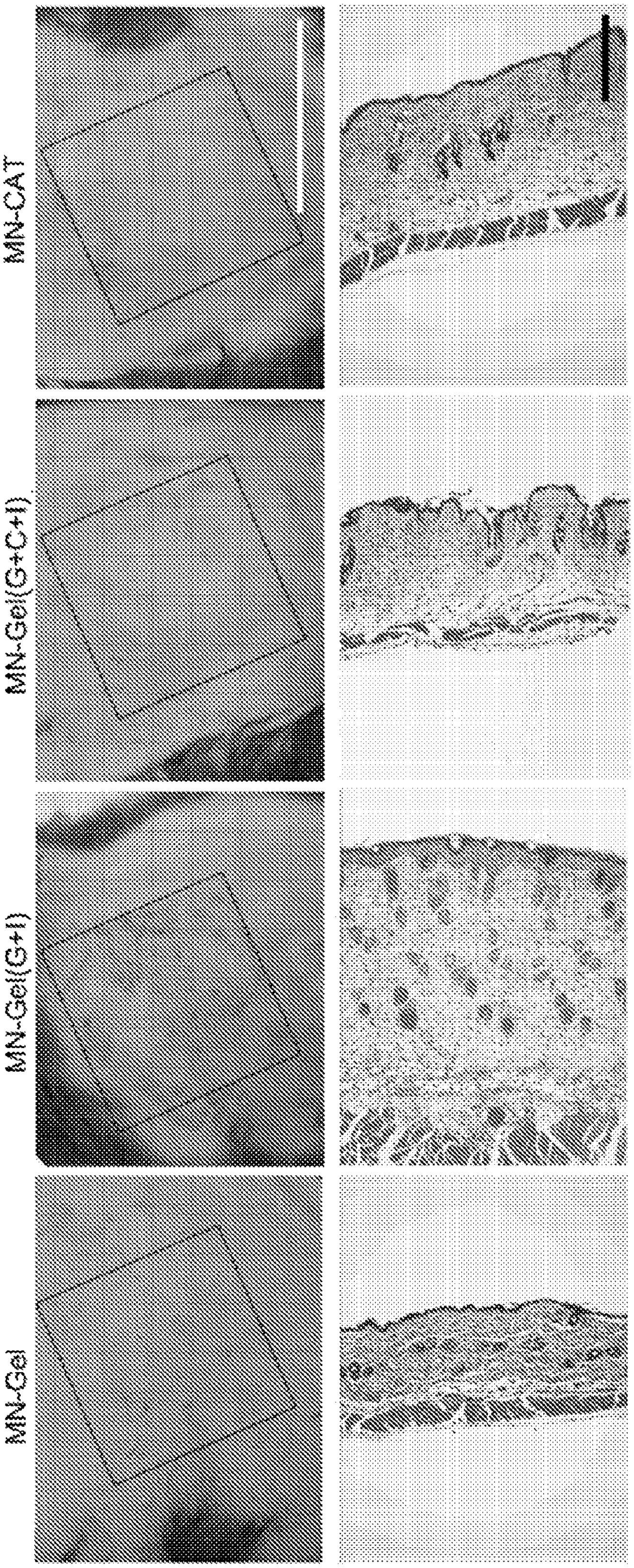
FIGS. 5A-5C. In vivo biocompatibility studies of MN-CAT arrays for diabetes treatment.
Figure 5B:
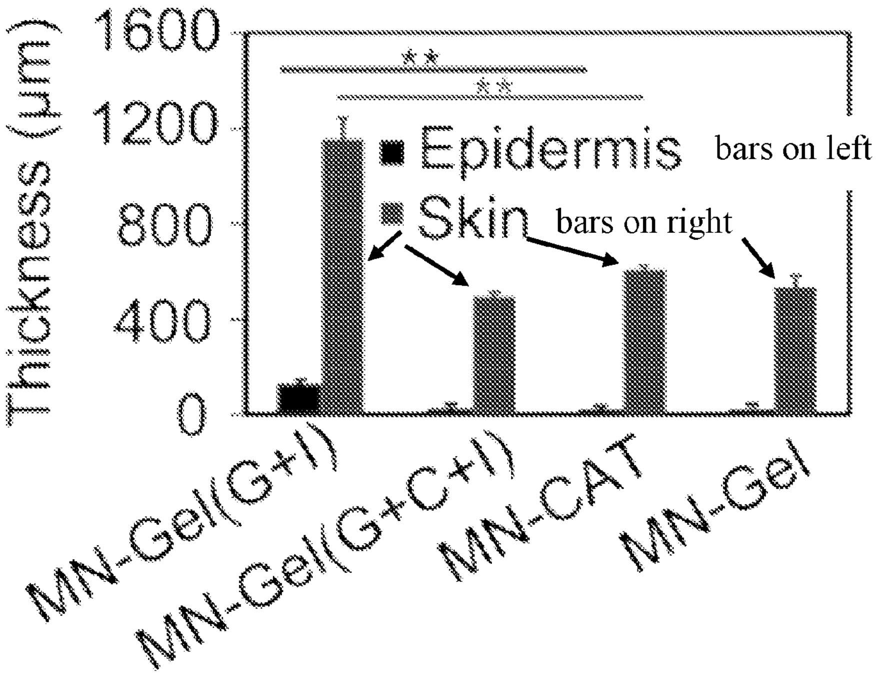
Figure 5C:
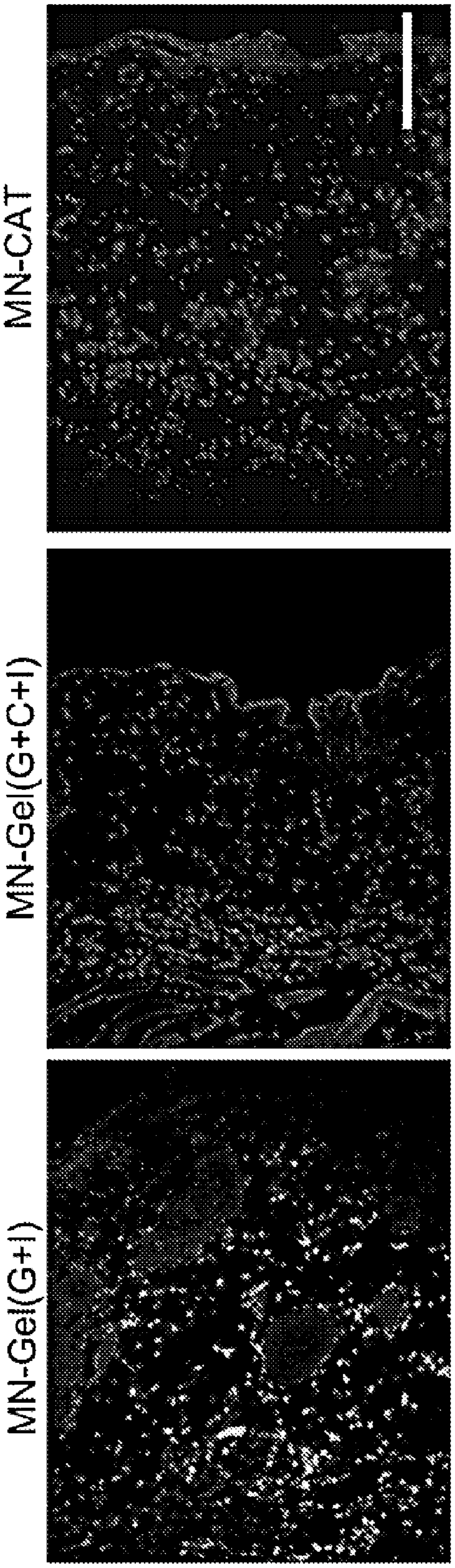
Figure 20:
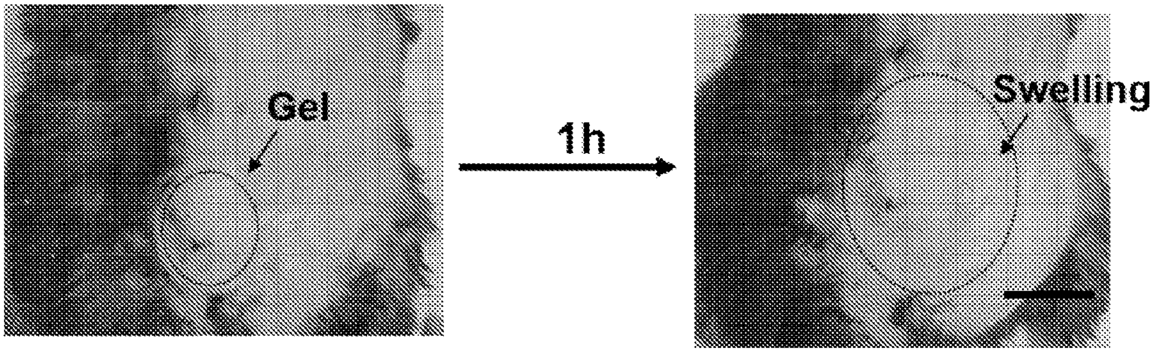
FIG. 20. Skin bubbling induced by subcutaneously injected Gel-(G+I). left: the site of gel inoculation; right: skin swelling observed 1 h post-inoculation. Scale bar, 1 cm.

The reaction between the phenylboronic acid and $H_2O_2$ alleviates the harm of generated $H_2O_2$ to surrounding tissues. However, any excessive unreacted $H_2O_2$ still carries potential to be harmful. Compared to the skin treated with MN-Gel (FIG. 5*a*), obvious inflammation was observed for mice treated with MN-Gel(G+I). Similar phenomenon was observed for skins treated with directly subcutaneously injected gel (FIG. 20). In a sharp contrast, almost no visible inflammation was observed on skins of mice treated with MN-CAT and MN-Gel(G+C+I) (FIG. 5*a*). These findings were reinforced in hematoxylin and eosin (H&E) staining results. Compared with skin treated with MN-Gel, skin samples treated with MN-Gel(G+I) showed obvious neutrophil infiltration, indicating a pathophysiological response and tissue damage induced by the generated $H_2O_2$.[27] However, greatly reduced neutrophil infiltration was observed in skin of mice treated with MN-Gel (G+C+I) and MN-CAT. The epidermal thickness and skin thickness for mice treated with both CAT-MN and MN-Gel(G+C+I) was comparable to that of skin treated with blank MN, but significantly thinner than they were for mice treated with MN-Gel(G+I) (FIG. 5*b*).[28] Moreover, the skin tissue stained with the in situ TUNEL assay clearly demonstrated the cell apoptosis in the skin sample treated with MN-Gel (G+I), whereas negligible cell death was observed in the skin tissue treated with CAT-loaded or coated MNs (FIG. 5*c*).

In summary, a core-shell gelated MN-array patch for glucose-responsive smart insulin delivery is disclosed. The MN-Gels were prepared via "solution-gelation" method involving layer-by-layer deposition of diluted solution. In vitro experiments showed that this crosslinked gel could rapidly release insulin when triggered by GOx-generated $H_2O_2$ in hyperglycemic conditions. Elevated local levels of $H_2O_2$ promotes both detachment of insulin from the gel matrix and degradation of matrix itself, which contributes to the effective glucose responsiveness. In vivo experiments indicated that the MN-CAT was highly effective in regulating BGLs and maintaining normoglycemia, while avoiding the critical risk of hypoglycemia. Importantly, utilization of CAT coating shows promise to significantly eliminate the inflammation caused by the generated $H_2O_2$. This bio-responsive core-shell MN array patch offers a broad platform for transdermal drug delivery with a physiological factor-controlled manner and enhanced biocompatibility.

Materials 4-(Bromomethyl) phenylboronic acid and 4-(hydroxylmethyl) phenylboronic acid were purchased from Boron Molecular. N,N,N',N'-tetramethyl-1,3-propanediamine (TMPA), 4-nitrobenzoyl chloride, triethylamine, PVA (89-98KDa, 99% hydrolysis) were purchased from Sigma-Aldrich. 4-nitrophenyl-(4,4,5,5-tetramethyl-1,3,2-dioxaborolan-2-yl)benzyl carbonate (NBC) was synthesized according to literature[29]. TSPBA was synthesized from TMPA and 4-(Bromomethyl) phenylboronic acid. PVA methacrylate was synthesized from the esterification reaction between PVA and methacrylic anhydride. Insulin-NBC was synthesized from insulin and NBC in a mixed solvent of DMSO and NaHCO3 aqueous solution.

Methods

Synthesis of TSPBA.

4-(Bromomethyl) phenylboronic acid (1 g, 4.6 mmol) and N,N,N',N'-tetramethyl-1,3-propanediamine (0.2 g, 1.5 mmol) were mixed in DMF (40 mL) and stirred at 60° C. for 24 h. The mixture was poured into THF (100 mL), filtrated, and washed by THF (3×20 mL). After dried under vacuum overnight, pure TSPBA (0.6 g, yield 70%) was obtained. 1H-NMR (300 MHz, D2O, δ): 7.677 (d, 4H), 7.395 (d, 4H), 4.409 (s, 4H), 3.232 (t, 4H), 2.936 (s, 6H), 2.81 (m, 2H).

Synthesis of Insulin-NBC.

Insulin (100 mg) was dissolved in 0.1 M NaHCO3 buffer solution (5 mL, pH=8.5) under stirring. To the above solution, 5 mL DMSO solution containing 20 mg NBC was added. The reaction mixtures were then stirred at room temperature overnight, followed by pH adjustment to precipitate insulin-NBC. The product was purified preparative using high scale performance liquid chromatography (HPLC, Agilent).

Synthesis of PVA Methacrylate.

PVA (1 g) and methacrylic anhydride (1 g) were dissolved in DMSO (20 mL) containing triethylamine (1 g). The solution was stirred overnight at room temperature. PVA methacrylate was precipitated upon addition of THF and washed three times. The product was dried under vacuum.

Rhodamine B or FITC Labeled Insulin or CAT.

Rhodamine B isothiocyanate (0.5 mg) dissolved in DMSO (1 mL) was added to insulin (20 mg) dissolved in NaHCO3 (10 mM, 1 mL). The mixture was stirred overnight and dialysis against DI H2O (3×2 L). The result solution was lyophilized to obtain rhodamine B labeled insulin. Other fluorescence labeled proteins were obtained with the same methods. The fluorescently labeled insulin or CAT were used in the same way as the one not labeled and the fluorescence images were taken on a fluorescence microscopy (Olympus, 1X71).

Insulin Release from PVA Methacrylate Gel.

Insulin or insulin-NBC was dissolved in H2O containing PVA methacrylate, and photo initiator (Irgacure 2959; 5% wt/vol) was added. This solution was assigned to three tubes, and exposed to UV light (360 nm) for 30 s for gelation. After the 30 s gelation, another 1 mL PBS and predetermined amount of $H_2O_2$ was added. At predetermined time intervals, solution (10 µL each tube) was withdrawn and stained with Coomassie blue (200 µL). The absorbance at 595 nm was detected on an Infinite 200 PRO multimode plate reader (TecanGroup Ltd.). The insulin content was calibrated by a standard curve.

GOx NG Release from PVA Methacrylate Gel.

Native GOx or GOx-NG was dissolved in H2O containing PVA methacrylate, and initiator (Irgacure 2959; 5% wt/vol) was added. This solution was assigned to one of three tubes, and exposed to UV light (360 nm) for 30 s. Then, another 1 mL PBS was added. At predetermined time intervals, solution (10 μL each tube) was withdrawn, and added to Coomassie blue (200 μL). The absorbance at 595 nm was detected on an Infinite 200 PRO multimode plate reader (TecanGroup Ltd.). The GOx concentration was calibrated by a standard curve.

$H_2O_2$ Generation Rate Assay in Glucose Solution in the Presence of GOx.

The $H_2O_2$ concentration was determined using a fluorometric hydrogen peroxide assay kit according to the manufacturer's protocol (Sigma-Aldrich). Glucose solutions (100 or 400 mg/dL) containing GOx (0.2 mg/mL) were incubated at 37° C. Samples (10 μL each tube) were withdrawn and diluted at timed intervals and the fluorescence intensity was detected.

Preparation of Insulin-NBC Loaded PVA-TSPBA Gel.

PVA-TSPBA gel was prepared by mixing PVA and TSPBA together. PVA (10 wt % in H2O, 100 μL) and insulin-NBC (10 wt % in H2O, 30 μL) were mixed first, followed by the addition of TSPBA (10 wt % in H2O, 30 μL) to fabricate a tough gel. During in vitro insulin release experiment, this gel was cut into pieces and incubated under different conditions.

In Vitro Insulin Release from PVA-TSPBA Gels.

Insulin-NBC loaded PVA-TSPBA gels were equally divided to centrifuge tubes containing 1 mL 10 mM PBS at pH 7.4. Various amounts of glucose (0, 100 or 400 mg/dL final concentration) and GOx (0.2 mg/mL) were added to the solution. At predetermined time intervals, solution (10 μL each tube) was withdrawn, stained with Coomassie blue (200 μL) and the absorbance at 595 nm was detected on an Infinite 200 PRO multimode plate reader (Tecan Group Ltd.). The insulin concentration was calibrated by a standard curve.

Fabrication of Microneedle Array Patch (with MN-CAT as an Example).

All of the MNs in this study were fabricated using five uniform silicone molds from Blueacre Technology Ltd. Each MN had a round base of 300 μm in diameter, which tapers over a height of 600 μm to a tip radius of around 5 μm. The MNs were arranged in a 20×20 array with 600 μm tip-tip spacing. First, diluted aqueous solutions of PVA (3.5 wt % in H2O, 450 μL), TSPBA (3.5 wt % in H2O, 150 μL) and CAT-NG (1 mg in 400 μL H2O) were prepared and mixed together. After deposition in a silicone mold, the solution was kept under reduced vacuum for 30 minutes and then transferred to a Hettich Universal 32R centrifuge for 20 min at 500 rpm to compact gel solution into MN cavities to form a membrane on the mold. Then, diluted aqueous solutions of PVA, methacrylated PVA, TSPBA, GOx-NG and photoinitiator (Irgacure 2959; 5% wt/vol) were loaded into mold and this procedure was repeated for several times until predetermined amount of insulin-NBC gel were loaded. Finally, 2 mL HA (4 wt % in H2O) was filled in each micromold surrounded by silver adhesive tape and dried under vacuum for 2 days. After the desiccation, the MN arrays were carefully separated from the silicone mold and the MNs underwent cross-linking polymerization via UV irradiation (wavelength of 365 nm) for a short period. The morphology of the MNs was characterized on an FEI Verios 460L field-emission scanning electron microscope.

The Mechanical Strength Test.

The mechanical strength of microneedles with a stress-strain gauge was determined by pressing a stainless steel plate against microneedles on an MTS 30G tensile testing machine. The initial gauge was 2.00 mm between the tips of microneedle and the plate, with 10.00 N as the load cell capacity. The speed of the plate approaching microneedles was set as 0.1 mm/s. The failure force of microneedles was recorded as the force at which the needle began to buckle.

In Vitro Skin Penetration Test.

To evaluate the in vitro skin penetrating ability of MNs, the MNs were inserted into the skin of the mouse for 10 min. The skin was stained with trypan blue for 10 min before imaging by optical microscopy (Leica EZ4 D stereomicroscope).

The Sample Size Calculated by Power Analysis: G*Power 3.1.

The experiments were not use a method of randomization. The investigators were not blinded to allocation during experiments and outcome assessment.

In Vivo Studies Using Streptozotocin-Induced Diabetic Mice.

The in vivo efficacy of both MN-array patches and gels for diabetes treatment was evaluated on streptozotocin-induced adult diabetic mice (male C57B6, age 8 wk; Jackson Laboratory). The animal study protocol was approved by the Institutional Animal Care and Use Committee at North Carolina State University and the University of North Carolina at Chapel Hill. The plasma glucose was measured from tail vein blood samples (~3 μL) of mice using the Clarity GL2Plus glucose meter (Clarity Diagnostics). Mouse glucose levels were monitored for two days before drug administration. Five mice for each group were selected to be treated using MN or native insulin. The glucose level of each mouse was monitored until stabilization. For mice treated with insulin-NBC loaded gels, PVA (10 wt % in H2O), insulin-NBC (50 μg in 10 μL H2O) and GOx-NG ((3 μg in 5 μL H2O), TSPBA (10 wt % in H2O) were consecutively injected subcutaneously to form the gel in situ.

Statistical Analysis.

Differences in blood glucose levels between the treated groups and controlled groups were determined by unpaired student's t-test. The results were considered statistically significant if the two-tailed P-values were less than 0.05. The statistical approach remained consistent throughout all analyses.

REFERENCES

[1] a) R. Mo, T. Jiang, J. Di, W. Tai, Z. Gu, Chem Soc Rev 2014, 43, 3595; b) O. Veiseh, B. C. Tang, K. A. Whitehead, D. G. Anderson, R. Langer, Nat Rev Drug Discov 2015, 14, 45.

[2] Y. Ohkubo, H. Kishikawa, E. Araki, T. Miyata, S. Isami, S. Motoyoshi, Y. Kojima, N. Furuyoshi, M. Shichiri, Diabetes Res Clin Pract 1995, 28, 103.

[3] D. R. Owens, B. Zinman, G. B. Bolli, Lancet 2001, 358, 739.

[4] E. Cengiz, J. L. Sherr, S. A. Weinzimer, W. V. Tamborlane, Expert Rev Med Devices 2011, 8, 449.

[5] B. W. Bequette, Diabetes Technol Ther 2005, 7, 28.

[6] a) K. M. Bratlie, R. L. York, M. A. Invernale, R. Langer, D. G. Anderson, Adv Healthc Mater 2012, 1, 267; b) C. R. Gordijo, K. Koulajian, A. J. Shuhendler, L. D. Bonifacio, H. Y. Huang, S. Chiang, G. A. Ozin, A. Giacca, X.

Y. Wu, Adv Funct Mater 2011, 21, 73; c) C. M. Hassan, F. J. Doyle, N. A. Peppas, Macromolecules 1997, 30, 6166.

[7] Z. Gu, A. A. Aimetti, Q. Wang, T. T. Dang, Y. Zhang, O. Veiseh, H. Cheng, R. S. Langer, D. G. Anderson, ACS Nano 2013, 7, 4194.

[8] Z. Gu, T. T. Dang, M. Ma, B. C. Tang, H. Cheng, S. Jiang, Y. Dong, Y. Zhang, D. G. Anderson, ACS Nano 2013, 7, 6758.

[9] J. Yu, Y. Zhang, Y. Ye, R. DiSanto, W. Sun, D. Ranson, F. S. Ligler, J. B. Buse, Z. Gu, Proc Natl Acad Sci USA 2015, 112, 8260.

[10] W. Tai, R. Mo, J. Di, V. Subramanian, X. Gu, J. B. Buse, Z. Gu, Biomacromolecules 2014, 15, 3495.

[11] a) K. Podual, F. J. Doyle Iii, N. A. Peppas, J Control Release 2000, 67, 9; b) K. Zhang, X. Y. Wu, J Control Release 2002, 80, 169; c) K. Podual, F. J. Doyle, N. A. Peppas, Polymer 2000, 41, 3975.

[12] a) Y. Dong, W. Wang, O. Veiseh, E. A. Appel, K. Xue, M. J. Webber, B. C. Tang, X.-W. Yang, G. C. Weir, R. Langer, D. G. Anderson, Langmuir 2016, 32, 8743; b) A. Matsumoto, T. Kurata, D. Shiino, K. Kataoka, Macromolecules 2004, 37, 1502; c) D. Shiino, Y Murata, A. Kubo, Y. J. Kim, K. Kataoka, Y. Koyama, A. Kikuchi, M. Yokoyama, Y. Sakurai, T. Okano, J Control Release 1995, 37, 269; d) A. Matsumoto, R. Yoshida, K. Kataoka, Biomacromolecules 2004, 5, 1038; e) K. Kataoka, H. Miyazaki, M. Bunya, T. Okano, Y. Sakurai, J Am Chem Soc 1998, 120, 12694.

[13] D. H. Chou, M. J. Webber, B. C. Tang, A. B. Lin, L. S. Thapa, D. Deng, J. V. Truong, A. B. Cortinas, R. Langer, D. G. Anderson, Proc Natl Acad Sci USA 2015, 112, 2401.

[14] a) F. Liu, S. C. Song, D. Mix, M. Baudys, S. W. Kim, Bioconjug Chem 1997, 8, 664; b) S. Joel, K. B. Turner, S. Daunert, ACS Chem Biol 2014, 9, 1595.

[15] G. Saravanakumar, J. Kim, W. J. Kim, Adv Sci 2016.

[16] W. A. Broom, C. E. Coulthard, M. R. Gurd, M. E. Sharpe, Br J Pharmacol Chemother 1946, 1, 225.

[17] S. Kitano, Y. Koyama, K. Kataoka, T. Okano, Y. Sakurai, J Control Release 1992, 19, 161.

[18] X. Liu, J. Xiang, D. Zhu, L. Jiang, Z. Zhou, J. Tang, X. Liu, Y. Huang, Y Shen, Adv Mater 2016, 28, 1743.

[19] M. Wang, S. Sun, C. I. Neufeld, B. Perez-Ramirez, Q. Xu, Angew Chem hit Ed Engl 2014, 53, 13444.

[20] C. De Duve, P Baudhuin, Physiol Rev 1966, 46, 323.

[21] M. Piest, X. L. Zhang, J. Trinidad, J. F. J. Engbersen, Soft Matter 2011, 7, 11111.

[22] N. A. Burns, M. A. Naclerio, S. A. Khan, A. Shojaei, S. R. Raghavan, JRheol 2014, 58, 1599.

[23] G. Springsteen, B. Wang, Tetrahedron 2002, 58, 5291.

[24] Y. Yamamoto, H. Koma, T. Yagami, NeuroToxicology 2015, 49, 86.

[25] a) O. Olatunji, D. B. Das, M. J. Garland, L. Belaid, R. F. Donnelly, Journal Of Pharmaceutical Sciences 2013, 102, 1209; b) S. P. Davis, B. J. Landis, Z. H. Adams, M. G. Allen, M. R. Prausnitz, J Biomech 2004, 37, 1155.

[26] I. C. Lee, J.-S. He, M.-T. Tsai, K.-C. Lin, J Mater Chem B 2015, 3, 276.

[27] Y. Liu, J. Du, M. Yan, M. Y. Lau, J. Hu, H. Han, O. O. Yang, S. Liang, W. Wei, H. Wang, J. Li, X. Zhu, L. Shi, W. Chen, C. Ji, Y. Lu, Nat Nano 2013, 8, 187.

[28] X. J. Jin, E. J. Kim, I. K. Oh, Y. K. Kim, C. H. Park, J. H. Chung, J Korean Med Sci 2010, 25, 930.

[29] J. L. Major Jourden, S. M. Cohen, Angew Chem Int Ed Engl 2010, 49, 6795.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A microneedle patch, comprising:
- a plurality of microneedles each having a base end and a tip; and
- a substrate to which the base ends of the microneedles are attached;
- wherein the microneedles comprise:
  - a shell, comprising:
  - a first poly (vinyl alcohol) (PVA) polymer cross-linked with a first peroxide-sensitive linker; and
  - a peroxide scavenging enzyme encapsulated within a first nanogel, wherein the first nanogel is embedded in the first PVA polymer;
  - and
  - a core, comprising:
  - a second poly (vinyl alcohol) (PVA) polymer cross-linked with a second peroxide-sensitive linker;
  - a glucose-responsive agent encapsulated within a second nanogel, wherein the second nanogel is embedded in the second PVA polymer; and
  - a therapeutic agent, wherein the therapeutic agent is covalently attached to the second PVA polymer with a third peroxide-sensitive linker;
  - wherein the glucose-responsive agent comprises glucose oxidase; and
  - wherein the therapeutic agent is insulin.

2. The microneedle patch of claim 1, wherein the first peroxide-sensitive linker comprises a boronic ester.

3. The microneedle patch of claim 1, wherein the first peroxide-sensitive linker is N1-(4-boronobenzyl)-N3-(4-boronophenyl)-N1,N1,N3,N3-tetramethylpropane-1,3-diaminium (TSPBA).

4. The microneedle patch of claim 1, wherein the second peroxide-sensitive linker comprises a boronic ester.

5. The microneedle patch of claim 1, wherein the second peroxide-sensitive linker is N1-(4-boronobenzyl)-N3-(4-boronophenyl)-N1,N1,N3,N3-tetramethylpropane-1,3-diaminium (TSPBA).

6. The microneedle patch of claim 1, wherein the third peroxide-sensitive linker comprises a boronic ester.

7. The microneedle patch of claim 1, wherein the third peroxide-sensitive linker is 4-nitrophenyl-(4,4,5,5-tetramethyl-1,3,2-dioxaborolan-2-yl) benzyl carbonate (NBC).

8. The microneedle patch of claim 1, wherein the peroxide scavenging enzyme is catalase.

9. The microneedle patch of claim 1, wherein the microneedles further comprise hyaluronic acid (HA).

10. A method of delivering a therapeutic agent to a subject, comprising:
- administering to the subject the microneedle patch of claim 1; and
- releasing the therapeutic agent from the microneedle patch in the presence of hyperglycemic levels of glucose.

11. The method of claim 10, wherein the subject has diabetes.

12. The method of claim 10, wherein the glucose-responsive agent produces a peroxide when exposed to hyperglycemic levels of glucose.

13. The method of any one of claim 10, wherein the method further comprises detaching the first peroxide-sensitive linker from the first PVA polymer upon exposure to the peroxide.

14. The method of claim 10, wherein the method further comprises detaching the second peroxide-sensitive linker from the second PVA polymer upon exposure to the peroxide.

15. The method of claim 10, wherein the method further comprises detaching the third peroxide-sensitive linker from the second PVA polymer upon exposure to the peroxide.

16. The method of claim 15, wherein the detaching of the third peroxide-sensitive linker from the second PVA polymer releases the therapeutic agent from the microneedle patch.

17. The method of claim 10, wherein the method further comprises reducing blood glucose levels.

18. The method of claim 10, wherein the method further comprises terminating release of the therapeutic agent prior to causing hypoglycemia.

* * * * *